US008986701B2

(12) United States Patent
Harrison

(10) Patent No.: US 8,986,701 B2
(45) Date of Patent: Mar. 24, 2015

(54) ENZYME PRODRUG CANCER THERAPY SELECTIVELY TARGETED TO TUMOR VASCULATURE AND METHODS OF PRODUCTION AND USE THEREOF

(71) Applicant: The Board of Regents of the University of Oklahoma, Norman, OK (US)

(72) Inventor: Roger G. Harrison, Norman, OK (US)

(73) Assignee: The Board of Regents of The University of Oklahoma, Norman, OK (US)

(*) Notice: Subject to any disclaimer, the term of this patent is extended or adjusted under 35 U.S.C. 154(b) by 154 days.

(21) Appl. No.: 13/655,913

(22) Filed: Oct. 19, 2012

(65) Prior Publication Data

US 2014/0044771 A1 Feb. 13, 2014

Related U.S. Application Data

(60) Division of application No. 12/721,125, filed on Mar. 10, 2010, now abandoned, and a continuation-in-part of application No. 12/502,011, filed on Jul. 13, 2009, now abandoned, which is a continuation of application No. 11/712,140, filed on Feb. 28, 2007, now abandoned, said application No. 12/502,011 is a continuation-in-part of application No. 10/870,832, filed on Jun. 17, 2004, now abandoned.

(60) Provisional application No. 61/158,783, filed on Mar. 10, 2009, provisional application No. 60/777,725, filed on Feb. 28, 2006, provisional application No. 60/479,106, filed on Jun. 17, 2003.

(51) Int. Cl.
| A61K 45/06 | (2006.01) |
| A61K 38/51 | (2006.01) |
| A61K 38/16 | (2006.01) |
| A61K 39/00 | (2006.01) |

(52) U.S. Cl.
CPC .............. *A61K 45/06* (2013.01); *A61K 38/51* (2013.01); *C12Y 404/01011* (2013.01); *C07K 2319/035* (2013.01); *C07K 2319/33* (2013.01); *A61K 38/16* (2013.01); *A61K 39/0011* (2013.01)
USPC ........................................ 424/184.1; 514/1.1

(58) Field of Classification Search
None
See application file for complete search history.

(56) References Cited

U.S. PATENT DOCUMENTS

| 4,473,646 A | 9/1984 | Guy et al. |
| 5,091,308 A | 2/1992 | Klegerman et al. |
| 5,126,134 A | 6/1992 | Heim et al. |
| 5,679,350 A | 10/1997 | Jankun et al. |
| 5,690,929 A | 11/1997 | Lishko et al. |
| 5,715,835 A | 2/1998 | Lishko et al. |
| 5,747,475 A | 5/1998 | Nordquist et al. |
| 5,759,542 A | 6/1998 | Gurewich |
| 5,767,298 A | 6/1998 | Daleke |
| 5,888,506 A | 3/1999 | Tan |
| 6,004,555 A | 12/1999 | Thorpe et al. |
| 6,051,230 A | 4/2000 | Thorpe et al. |
| 6,093,399 A | 7/2000 | Thorpe et al. |
| 6,132,729 A | 10/2000 | Thorpe et al. |
| 6,156,321 A | 12/2000 | Thorpe et al. |
| 6,231,854 B1 | 5/2001 | Yuying |
| 6,312,694 B1 | 11/2001 | Thorpe et al. |
| 6,319,702 B1 | 11/2001 | Smith et al. |
| 6,406,693 B1 | 6/2002 | Thorpe et al. |
| 6,451,312 B1 | 9/2002 | Thorpe |
| 6,491,894 B1 | 12/2002 | Ruoslahti et al. |
| 6,528,481 B1 | 3/2003 | Burg et al. |
| 6,576,239 B1 | 6/2003 | Ruoslahti et al. |
| 6,610,651 B1 | 8/2003 | Ruoslahti et al. |
| 6,749,853 B1 | 6/2004 | Thorpe et al. |
| 6,783,760 B1 | 8/2004 | Thorpe et al. |
| 6,818,213 B1 | 11/2004 | Thorpe et al. |
| 6,933,281 B2 | 8/2005 | Ruoslahti et al. |
| 7,067,109 B1 | 6/2006 | Thorpe et al. |
| 2002/0150984 A1 | 10/2002 | Mochly-Rosen et al. |
| 2003/0045496 A1* | 3/2003 | Miki et al. ............... 514/44 |
| 2004/0170620 A1* | 9/2004 | Thorpe et al. ......... 424/130.1 |
| 2006/0258584 A1 | 11/2006 | Lind et al. |

FOREIGN PATENT DOCUMENTS

WO 95/17908 7/1995

OTHER PUBLICATIONS

Tait et al, JBC 270:21594, 1995, IDS filed Aug. 1, 2013, #22.*
Yang et al, Cancer Res 64:6673-78, 2006.*
Song et al, Immunopharmacology and immunotoxicology 31:202-208, 2009.*
Hsu; "Tissue Culture Methods and Applications"; Kruse and Patterson, Eds, Academic Press, NY, see Abstract, p. 764; 1973.
Halpern, B.C., et al.; "The Effect of Replacement of Methionine by Homocystine on Survival of Malignant and Normal Adult Mammalian Cells in Culture"; Proc. Nat. Acad. Sci. USA; 71:1133-1136; 1974.
Embleton, et al.; Immunol. Ser.; 23:181-207; 1984.
Marquardt, H., et al.; "Rat Transforming Growth Factor Type I: Structure and Relation to Epidermal Growth Factor"; Science; 223:1979-1081; 1984.
Stoppelli, M.P., et al.; "Differentiation-Enhanced Binding of the Amino-Terminal Fragment of Human Urokinase Plasminogen Activator to a Specific Receptor on U937 Monocytes"; Proc. Natl. Acad. Sci. USA; 82:4939-4943; 1985.
Appella, E., et al.; "The Receptor-Binding Sequence of Urokinase"; J. Biol. Chem.; 262:4437-4440; 1987.
Kimmel, et al.; J. Neurosurg.; 66:161-171; 1987.
Muraguchi, A., et al.; "The Essential Role of B Cell Stimulatory Factor 2 (BSF-2/IL-6) for the Terminal Differentiation of B Cells"; J. Exp. Med.; 167:332-344; 1988.
Argos; "An Investigation of Oligopeptides Linking Domains in Tertiary Structures and Possible Candidates for General Gene Fusion"; J. Mol. Biol.; 211:943-958; see figure 2, p. 950; 1990.

(Continued)

*Primary Examiner* — Lei Yao
(74) *Attorney, Agent, or Firm* — Dunlap Codding, P.C.

(57) ABSTRACT

Methods of treating cancer by targeting tumor vasculature using an enzyme prodrug cancer therapy treatment are provided.

6 Claims, 5 Drawing Sheets

(56) References Cited

OTHER PUBLICATIONS

Figure 1:
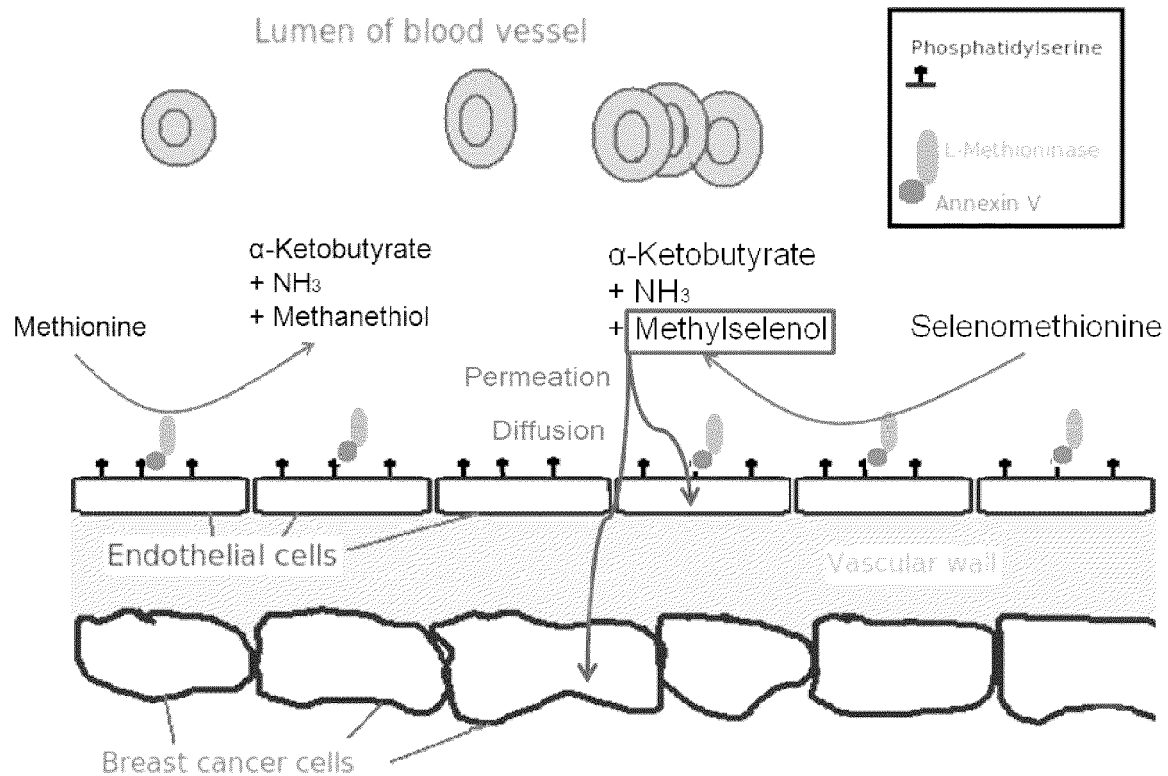

Chen, L., et al.; "IL-6 Receptors and Sensitivity to Growth Inhibition by IL-6 in Clones of Human Breast Carcinoma Cells"; J. Biol. Regul. Homeost. Agents; 5:125-136; 1991.
Prior, T.I., et al.; "Cytotoxic Activity of a Recombinant Fusion Protein Between Insulin-Like Growth Factor I and *Pseudomonas* Exotoxin"; Cancer Res.; 51:174-180; 1991.
Utsugi, et al.; "Elevated Expression of Phosphatidylserine in the Outer Membrane Leaflet of Human Tumor Cells and Recognition by Activated Human Blood Monocytes"; Cancer Res.; 51(11):3062-6; 1991.
Boon; Adv. Can. Res.; 58:177-210; 1992.
Rao, et al.; "Binding of Annexin V to a Human Ovarian Carcinoma Cell Line" (OC-2008); "Contrasting Effects on Cell Surface Factor VIIa/Tissue Factor Activity and Prothrombinase Activity"; Thromb Res.; 67(5):517-31; 1992.
Pastan, I., et al.; "Recombinant Toxins as Novel Therapeutic Agents"; Annu. Rev. Biochem.; 61:331-354; 1992.
Drexler, et al.; Leukemia and Lymphoma; 9:1-25; 1993.
Abbaszadegan, M.R., et al.; Cancer Res.; 54:4676-4679; 1994.
Dermer; Bio/Technology; 12:320; 1994.
Phillips, P.C., et al.; "Transforming Growth Factor-α—*Pseudomonas* Exotoxin Fusion Protein (TGF-α-PE38) Treatment of Subcutaneous and Intracranial Human Glioma and Medulloblastoma Xenografts in Athymic Mice"; Cancer Res.; 54:1008-1015; 1994.
Stanton, P., et al.; Br. J. Cancer; 70:427-433; 1994.
Kobayashi, et al.; J. Biol. Chem.; 270(14):8361-8366; 1995.
Tait, et al.; Prourokinase-Annexin V Chimeras; The Journal of Biological Chemistry; vol. 270, No. 37, pp. 21594-21599; 1995.
Tan, et al.; "Serum Methionine Depletion without Side Effects by Methioninase in Metastatic Breast Cancer Patients"; Anticancer Research; 16:3937-3942; 1996.
Kokkinakis, D.M., et al.; "Regulation of $O^6$-Methylguanine-DNA Methyltransferase by Methionine in Human Tumor Cells"; Br. J. Cancer; 75:779-788; 1997.
Tan, et al.; "Recombinant Methioninase Infusion Reduces the Biochemical Endpoint of Serum Methionine with Minimal Toxicity in High-Stage Cancer Patients"; Anticancer Research; 17:3857-3860; 1997.
Gooch, J.L., et al.; "Interleukin 4 Inhibits Growth and Induces Apoptosis in Human Breast Cancer Cells"; Cancer Res.; 58:4199-4205; 1998.
Tan, et al.; "Polyethylene Glycol Conjugation of Recombinant Methioninase for Cancer Therapy"; Protein Expression and Purification; 12:45-52; 1998.
Iehle, C., et al.; J. Steroid Biochem. Mol. Biol.; 68:189-195; 1999.
Bodey, et al.; Anticancer Res.; 20:2665-2676; 2000.
Kunkel, P., et al.; Neuro-Oncology; 3(2):82-88; 2001.
Taylor, et al.; "A Phase I and Pharmacodynamic Evaluation of Polyethylene Gloycol-Conjugated L-Asparaginase in Patients with Advanced Solid Tumors"; Cancer Chemother. Pharmacol.; 47:83-88; 2001.
Ran, et al.; Phosphatidylserine is a Marker of Tumor Vasculature and a Potential Target for Cancer Imaging and Therapy; Int. J. Radiation Oncology Biol. Phys. vol. 54, No. 5, pp. 1479-1484; 2002.
Ran, et al.; Increased Exposure of Anionic Phospholipids on the Surface of Tumor Blood Vessels; Cancer Res. 62, 6132-6140; 2002.
Yang, et al.; Enhancing the Anticoagulant Potency of Soluble tissue Factor Mutants by Increasing their Affinity to Factor VIIIa; Thromb Haemost, 87:450-8; 2002.
Zaslav, A.L., et al.; Amer. J. Medical Genetics; 107:174-176; 2002.
Peron, et al.; "Targeting of a Novel Fusion Protein Containing Methioninase to the Urokinase Receptors to Inhibit Breast Cancer Cell Migration and Proliferation"; Cancer Chemother. Pharmacol.; 52:270-276; 2003.
Van Dyke, D.L., et al.; Cancer Genetics and Cytogenetics; 142:137-141; 2003.
Palwai, et al.; "Targeting L-Methioninase to Human Cancer Cells"; OCAST Research Conference; Apr., 2004.
Palwai, et al.; "L-Methioninase Fusion Protein Targeted to Human Cancer Cells"; Poster presentation at the 33$^{rd}$ Annual Biochemical Engineering Symposium, University of Nebraska-Lincoln; May 2004.
Pento, et al.; "Influence of a Methioninase Containing Fusion Protein Targeted too the Urokinase Receptors on Breast Cancer Metastasis in Nude Mouse Xenografts"; AACR Conference "Frontiers in Cancer Prevention Research"; Seattle, WA; Oct. 2004.
Tian, J., et al.; Physiol Genomics; 17:170-182; 2004.
Zips, et al.; In vivo; 19:1-8; 2005.
Zang, et al.; Internalizing Versus Non-internalizing Receptors for Targeting L-Methioninase to Cancer Cells; American Journal of Pharmacology and Toxicology 1(3):60-64; 2006.
Kaiser, Science; 313:1370; 2006.
Mellman, I.; The Scientist; 20(1):177-210; 2006.
Kenis, et al.; Cell. Mol. Life Sci.; 64:2859-2862; 2007.
Dumler, et al.; "Urokinase Activates the Jak/Stat Signal Trasduction Pathway in Human Vascular Endothelial Cells", Aarterioscler Thromb Vasc Biol 19:290-297; 1999.
Jafferali, S., et al.; "Insulin-Like Growth Factor-I and Its Receptor in the Frontal cortex, Hippocampus, and Cerebellum of Normal Human and Alzheimer Disease Brains"; Synapse 38:450-459; 2000.
Melton, R., et al.; "Antibody—Enzyme Conjugates for Cancer Therapy"; J. Natl Canc. Inst. 88(3/4):153-165; 1996.
Murata, T., et al.; "Two different IL-13 receptor chains are expressed in normal human skin fibroblasts, and IL-4 and IL-13 mediate signal transduction through a common pathway"; Intl. Immun. 10(8):1103-1110; 1998.
Seigfried, S., et al.; "Distrinct patterns of expression of keratinocyte growth factor and its receptor in endometrial carcinoma"; Cancer 79(6):1166-1171; 1997.
Vallera, D., et al.; "Targeting Urokinase-Type Plasminogen Activator Receptor on Human Glioblastoma Tumors With diphtheria Toxin Fusion Protein DTAT"; J. Natl Canc. Inst. 94(8):597-606; 2002.

\* cited by examiner

ENZYME PRODRUG CANCER THERAPY SELECTIVELY TARGETED TO TUMOR VASCULATURE AND METHODS OF PRODUCTION AND USE THEREOF

This application is a divisional of U.S. Ser. No. 12/721,125, filed Mar. 10, 2010, now abandoned; which claims benefit under 35 U.S.C. 119(e) of provisional application U.S. Ser. No. 61/158,783, filed Mar. 10, 2009. The '125 application is also a continuation-in-part of U.S. Ser. No. 12/502,011, filed Jul. 13, 2009, now abandoned; which is a continuation of U.S. Ser. No. 11/712,140, filed Feb. 28, 2007, now abandoned; which claims benefit under 35 U.S.C. 119(e) of U.S. Provisional Application No. 60/777,725, filed Feb. 28, 2006. The '011 application is also a continuation-in-part of U.S. Ser. No. 10/870,832, filed Jun. 17, 2004, now abandoned; which claims benefit under 35 U.S.C. 119(e) of U.S. Provisional Application No. 60/479,106, filed Jun. 17, 2003.

STATEMENT REGARDING FEDERALLY SPONSORED RESEARCH OR DEVELOPMENT

This invention was made with government support under Contract Number W81XWH-08-1-0722 awarded by the Department of Defense (DOD). The government has certain rights in the invention.

BACKGROUND OF THE PRESENTLY DISCLOSED AND CLAIMED INVENTIVE CONCEPT(S)

Although the rate of cancer incidence has declined since 1990, the number of people in the U.S. who are expected to die in 2004 from cancer is still expected to exceed half a million. The five most prevalent types of cancer in the U.S., ranked by the estimated number of new cases for the year 2004 (excluding base and squamous cell cancers of the skin), are as follows: prostate, female breast, lung and bronchus, colon and rectum, and urinary bladder. Breast cancer is the leading cause of cancer in U.S. women, with approximately 216,000 new cases diagnosed and 40,000 deaths per year.

Several modalities, including radiation, chemotherapy, and surgery, either alone or in combination, are being used for the treatment of cancer. Because of these treatments, most patients with skin cancer, and about half the people treated for internal cancers, are completely freed of their disease. However, the therapies now available for internal cancers often give rise to side effects so harmful that they compromise the benefits of treatment, and existing therapies for such internal cancers often fail in many cases. Radiation and surgery are limited in that they cannot treat widespread metastases that eventually form full fledged tumors at numerous sites. In the 1960's it was discovered that chemotherapy could cure some cancers when several drugs were given in combination. Unfortunately, the most common cancers (breast, lung, colorectal, and prostate cancer) are not yet curable with chemotherapy alone.

Enzyme prodrug therapy was proposed in the mid-1980's as a means of restricting the action of cytotoxic drugs to tumor sites, thereby increasing their efficacy and reducing their normal tissue toxicity. Enzyme prodrug therapy is a two-step approach. In the first step, a drug-activating enzyme is targeted to the tumor cells. In the second step, a nontoxic prodrug, a substrate of the exogenous enzyme that is not expressed in tumors, is administered systemically. The net gain is that a systemically administered prodrug can be converted to high local concentration of an active anticancer drug in tumors. The enzyme should be either of nonhuman origin or a human protein that is absent or expressed only at low concentrations in normal tissues. The enzyme prodrug systems developed to date have used antibodies to target the enzyme to the tumor, and this therapy has been called antibody-directed enzyme prodrug therapy (ADEPT). Drawbacks of ADEPT include poor accessibility of the enzyme/antibody conjugate to the tumor, the cost and difficulties with development and purification of antibodies, and immunogenicity of both the antibody and the enzyme (G. Xu and H. L. McLeod, 2001, Strategies for enzyme/prodrug cancer therapy, Clinical Cancer Research, 7:3314-3324).

Results obtained over the past 40 years have demonstrated that tumor cells of all types tested have an elevated growth requirement for methionine compared to normal cells (Miki et al., 2000). Numerous lines of cancer cells are unable to survive and grow when the amino acid methionine is replaced in the medium with homocystine. However, normal adult cell lines survive and grow well with this substitution. For example, Halpern et al. (1974) showed that breast carcinosarcoma and lymphatic leukemia cells did not retain viability after 20 days in media devoid of methionine but with added homocystine. On the other hand, normal liver fibroblasts, breast fibroblasts, and prostate fibroblasts grew normally under these same conditions. Further studies have shown that methionine-dependent cells arrest in the G2 and G1 phases of the cell cycle and subsequently die at methionine concentrations less than 5 µM regardless of high concentrations of homocystine precursors and folates (Kokkinakis et al., 1997a).

Subsequent to the tests of the effect of methionine on cancer and normal cells in cell culture, there have been in vivo tests of the effect of methionine depletion on cancer cells. One comprehensive study was performed on mice with human brain tumor xenografts (Kokkinakis et al., 1997b). With a combination of dietary restriction of methionine, homocysteine, and choline and synchronous treatments with intraperitoneal injections of L-methioninase (44 mg/kg per day of L-methioninase) and homocystine, tumor stasis was achieved in 100% of treated animals within four days of treatment, and regression was seen in one-third of animals after a 10-day period. The methioninase produced no toxicity in the mice.

However, the current methioninase experimental methodologies require large dosages of methioninase as well as methionine-, homocystine-, and choline-restricted diets.

Therefore, there is a need in the art for new and improved methods of targeting anticancer agents specifically to the surface of cancer cells, or specifically to the surface of blood vessels supplying the cancer cells. It is to such methods of targeting anticancer agents to the surface of cancer cells or blood vessels supplying the cancer cells, thereby requiring significantly lower dosages of anticancer agents than current methods, and thus overcoming the disadvantages and defects of the prior art, that the presently disclosed and claimed inventive concept(s) is directed.

BRIEF DESCRIPTIONS OF THE DRAWINGS

FIG. 1 graphically depicts the mechanism of action of enzyme prodrug therapy in accordance with the presently disclosed and claimed inventive concept(s). For the purposes of illustration, this depiction utilizes an L-methioninase-annexin V fusion protein. After injecting the L-methioninase-annexin V fusion protein in the blood stream, the annexin V portion of the fusion protein will ensure the specific binding to the phosphatidylserine exposed on the endothelial cells of the tumor vasculature, while the L-methioninase portion will act on the tumor in two ways. First, it will catalyze the conversion of the non-toxic prodrug SeMet into toxic methylselenol which, by means of permeation and diffusion, will go inside the cells and cause their death. Second, it will cut the methionine supply to the cancer cells by degrading it and depleting it from the vicinity of tumors.

Figure 2:
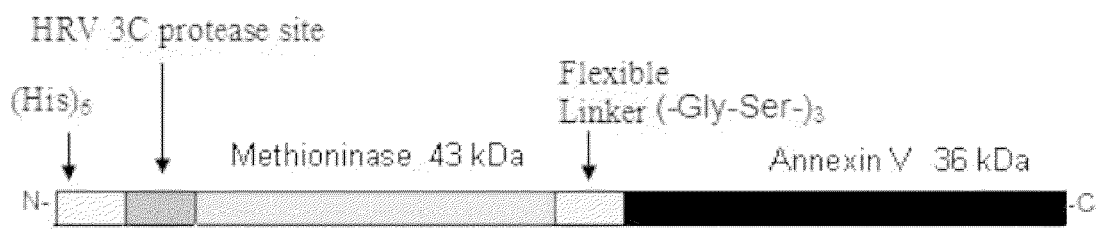

FIG. 2 graphically depicts the construction of the fusion protein in accordance with the presently disclosed and claimed inventive concept(s). When purified, the His-tag is used to selectively extract this protein from all the other proteins expressed by E. coli. The protease site is then used to remove the His-tag. The (Gly-Ser)$_3$ flexible linker is used to connect the L-methioninase subunit to the annexin V subunit without harming their respective conformations.

Figure 3:
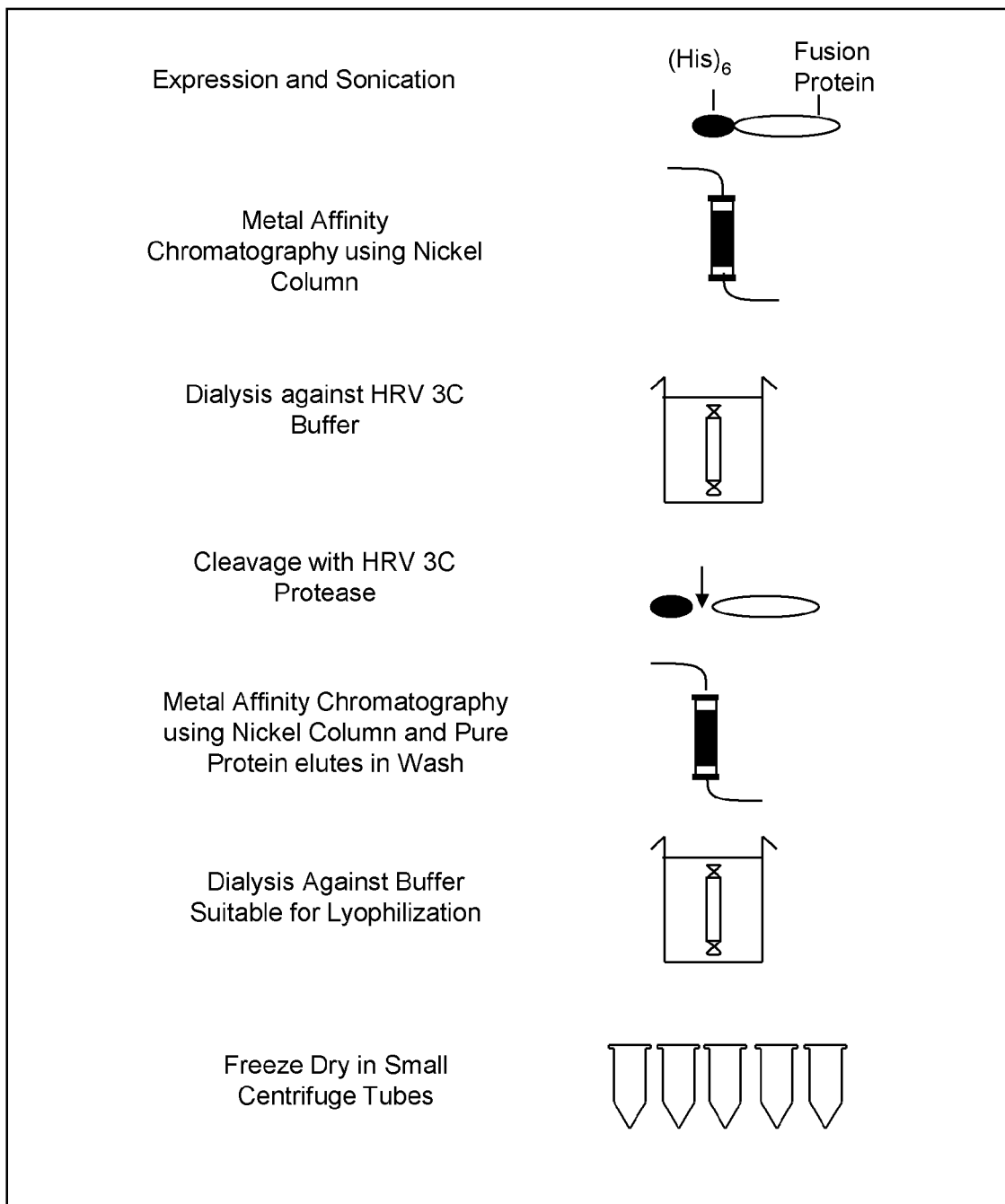

FIG. 3 graphically depicts a scheme for the purification of fusion proteins constructed in accordance with the presently disclosed and claimed inventive concept(s), wherein the purification utilizes a HisTrap column with immobilized nickel.

Figure 4:
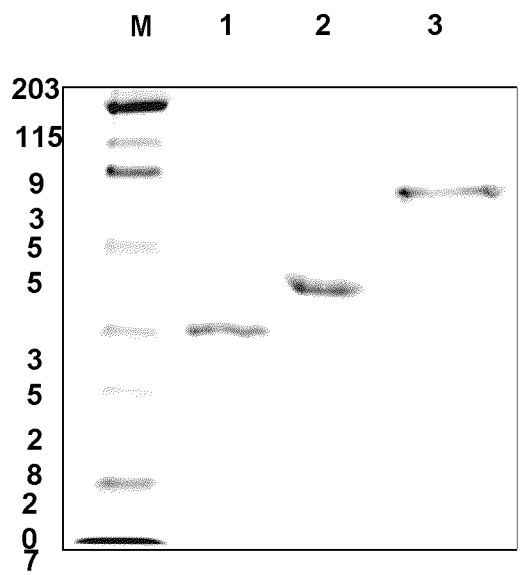

FIG. 4 illustrates SDS-PAGE analysis with Coomassie blue staining of three of the purified proteins constructed in accordance with the presently disclosed and claimed inventive concept(s). Lane 1, annexin V; lane 2, L-methioninase; lane 3, methioninase-annexin V fusion protein (Meth-AnnV). M marker proteins with molecular masses are indicated on the left in kiloDaltons.

Figure 5:
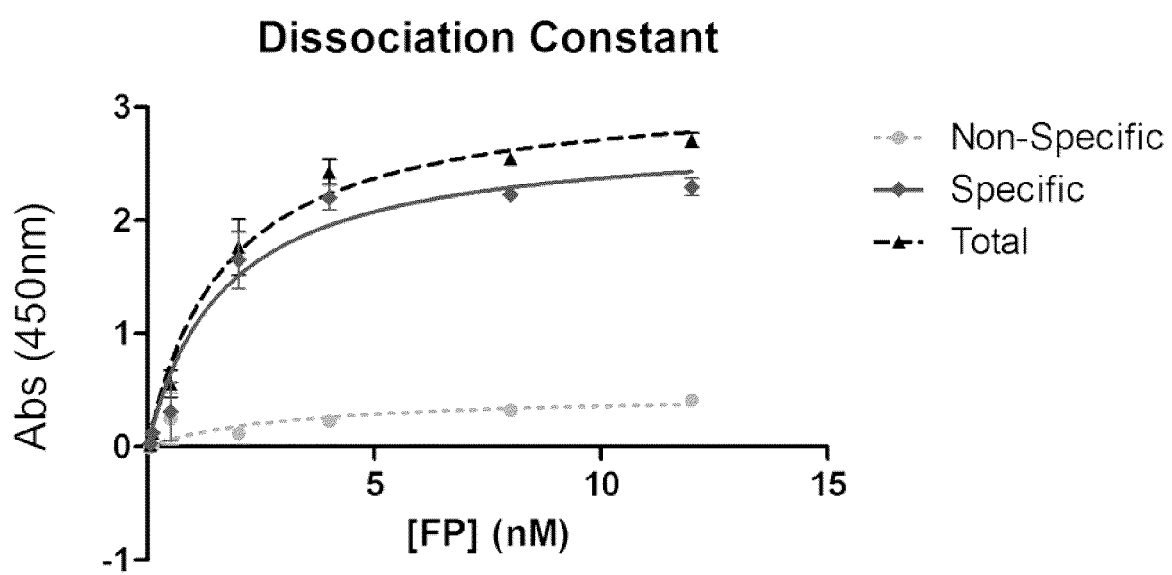

FIG. 5 graphically depicts a determination of Meth-AnnV fusion protein (FP) binding strength to exposed PS on endothelial cells. The FP was biotinylated, and streptavidin-HRP was used to quantify the binding. Total binding was obtained by having 2 mM of $Ca^{2+}$ in the binding buffer. Non-specific binding was obtained by removing the $Ca^{2+}$ for the binding buffer and replacing it with 5 mM of EDTA to chelate $Ca^{2+}$. Specific binding was obtained by subtracting the non-specific binding from the total binding. Bars indicate the standard error of the mean (SEM), n=3.

Figure 6:
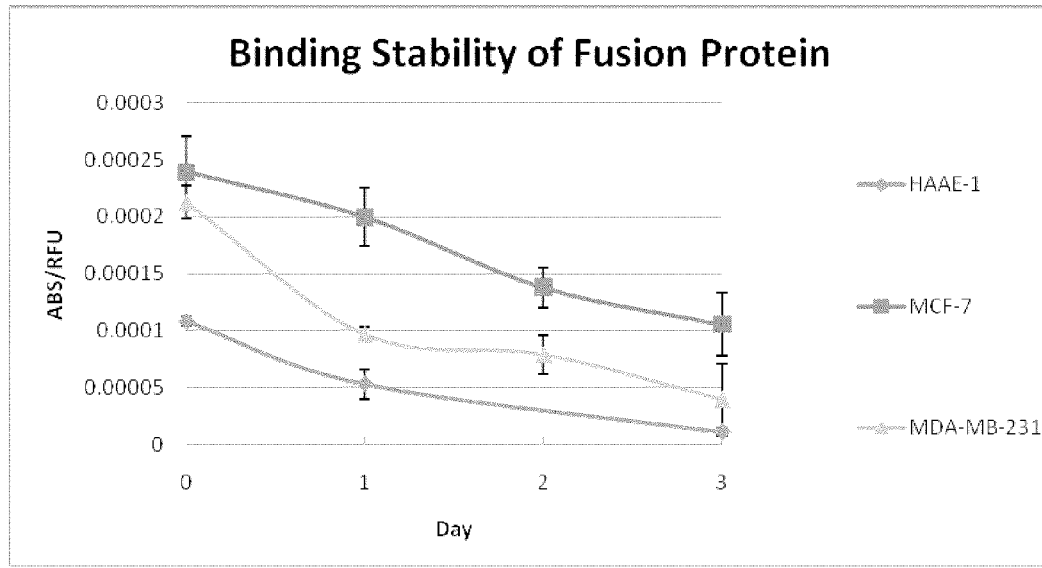

FIG. 6 graphically depicts binding stability of the Meth-AnnV fusion protein to three different cell lines. The Alamar Blue assay was performed each day, followed by the binding assay to determine the duration of binding of annexin V to the exposed PS on the surface of each cell line. FP was found to stay bound to the cell lines for at least 3 days, the period of the experiment. ABS is the absorbance at 450 nm that is measured in the binding assay. RFU is relative fluorescence units, measured by the Alamar Blue assay for cell viability. Bars indicate the standard error of the mean (SEM), n=3.

Figure 7:
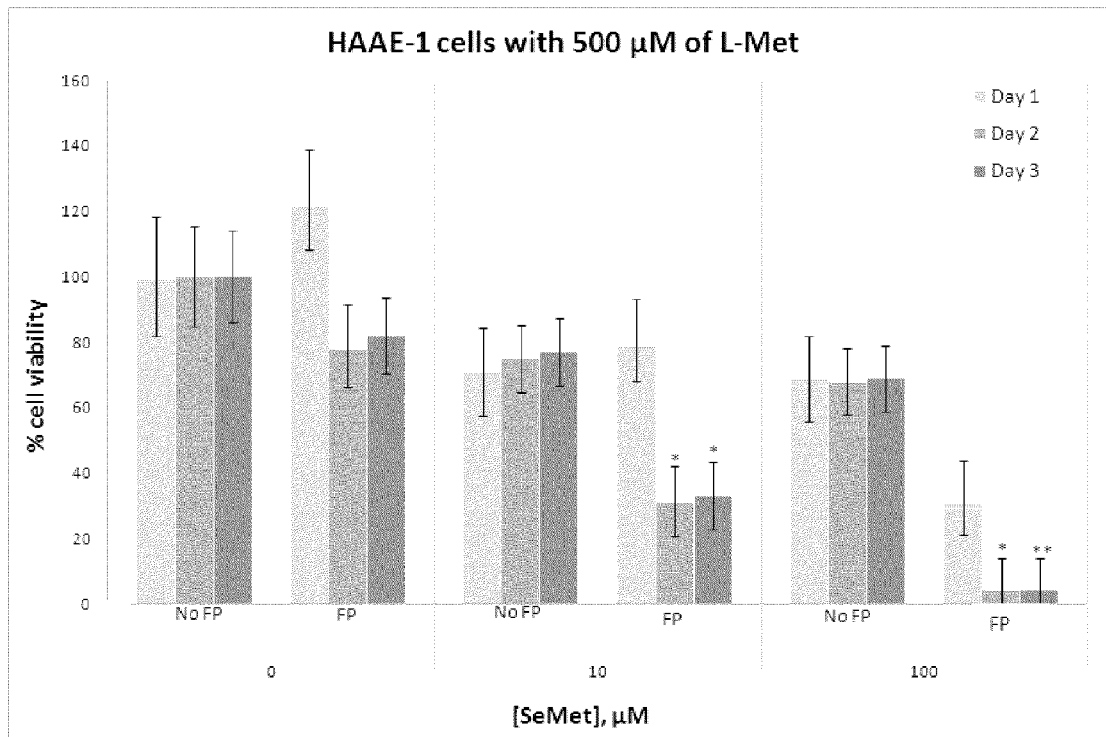

FIG. 7 illustrates the effect of SeMet conversion to methylselenol by Meth-AnnV on HAAE-1 endothelial cells. Cells were grown in medium adjusted to 500 µM of L-methionine. Cell viability was assessed using Alamar Blue assay and normalized to the control (i.e., no FP and no SeMet). A two-tailed T-test was performed for statistical analysis. Cells treated with different SeMet concentrations but with no FP were compared to the control, and statistical significance was represented with (#). Cells treated with different SeMet concentrations and FP were compared to cells that were treated with the same SeMet concentration but no FP, and statistical significance was represented with (*). $*p<0.05$; $**p<0.01$. Bars indicate the standard error of the mean (SEM), n=3.

Figure 8:
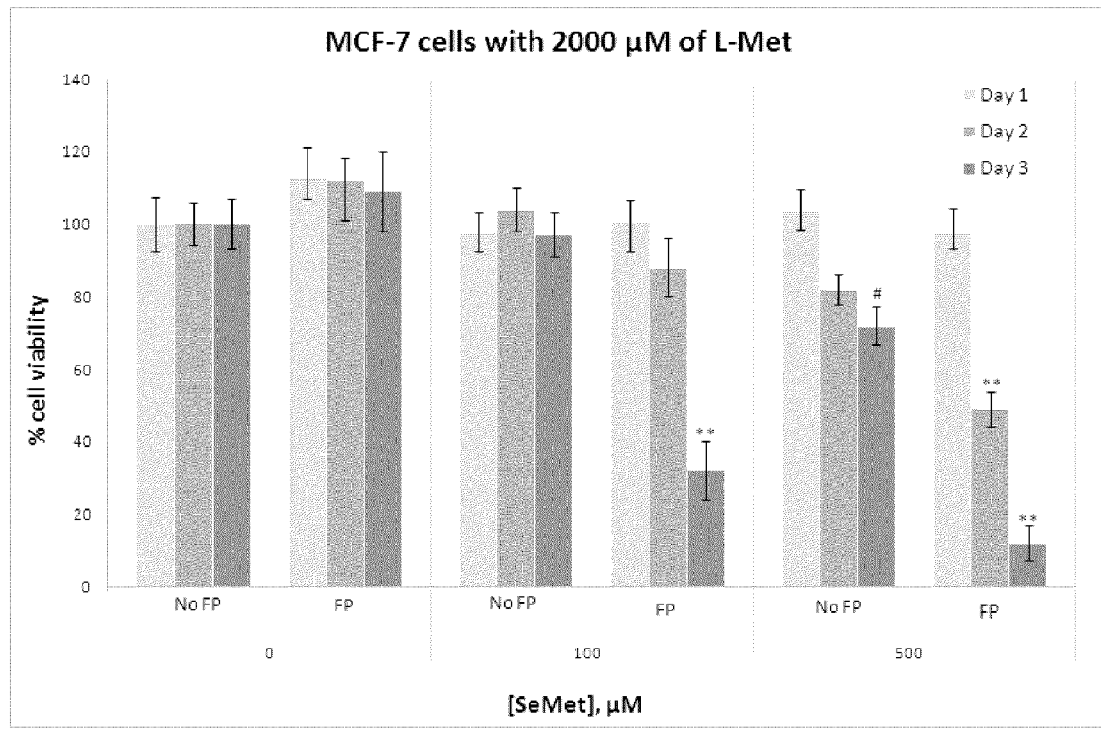

FIG. 8 illustrates the effect of SeMet conversion to methylselenol by Meth-AnnV on MCF-7 breast cancer cells. Cells were grown in medium adjusted to 2000 µM of L-methionine. Cell viability was assessed using Alamar Blue assay and normalized to the control (i.e., no FP and no SeMet). A two-tailed T-test was performed for statistical analysis. Cells treated with different SeMet concentrations but with no FP were compared to the control, and statistical significance was represented with (#). Cells treated with different SeMet concentrations and FP were compared to cells that were treated with the same SeMet concentration but no FP and statistical significance was represented with (*). $\#p<0.05$. $*p<0.05$; $**p<0.01$. Bars indicate the standard error of the mean (SEM), n=3.

Figure 9:
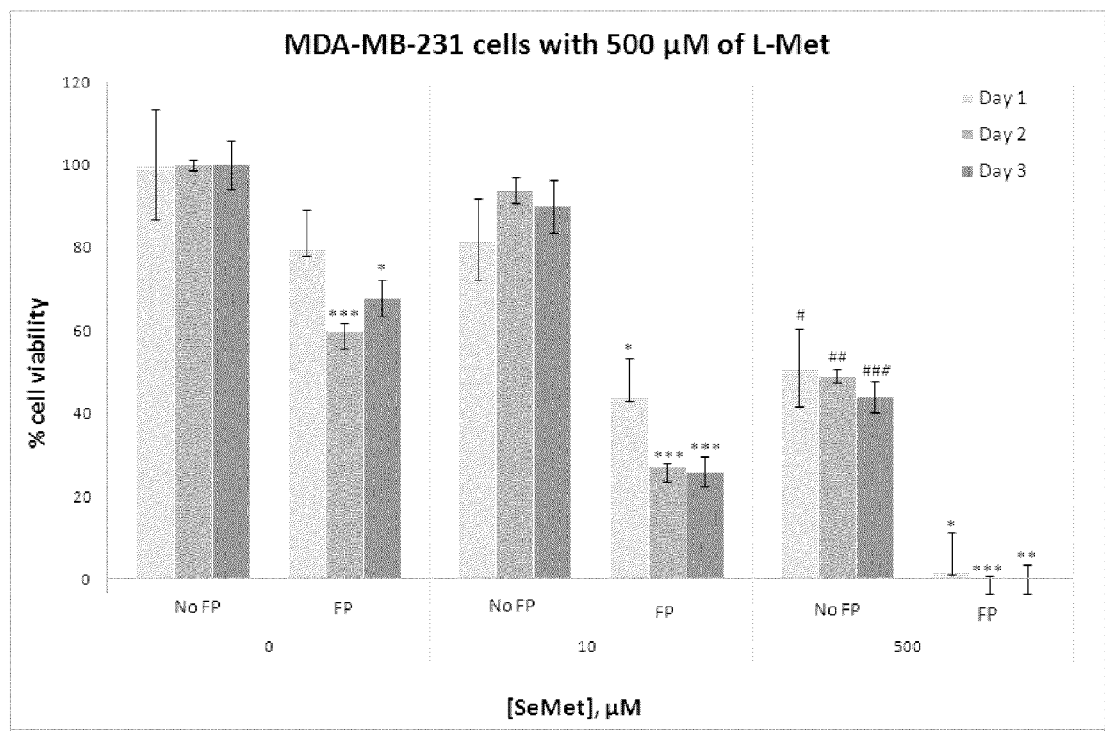

FIG. 9 illustrates the effect of SeMet conversion to methylselenol by Meth-AnnV on MDA-MB-231 breast cancer cells. Cells were grown in medium containing 500 µM of L-methionine. Cell viability was assessed using Alamar Blue assay and normalized to the control (i.e., no FP and no SeMet). A two-tailed T-test was performed for statistical analysis. Cells treated with different SeMet concentrations but with no FP were compared to the control, and statistical significance was represented with (#). Cells treated with different SeMet concentrations and FP were compared to cells that were treated with the same SeMet concentration but no FP and statistical significance was represented with (*). #, $*p<0.05$; ##, $p<0.01$; ###, $*p<0.001$. Bars indicate the standard error of the mean (SEM), n=3.

DETAILED DESCRIPTION OF THE PRESENTLY DISCLOSED AND CLAIMED INVENTIVE CONCEPT(S)

Before explaining at least one embodiment of the presently disclosed and claimed inventive concept(s) in detail by way of exemplary drawings, experimentation, results, and laboratory procedures, it is to be understood that the presently disclosed and claimed inventive concept(s) is not limited in its application to the details of construction and the arrangement of the components set forth in the following description or illustrated in the drawings, experimentation and/or results. The presently disclosed and claimed inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. *Molecular Cloning: A Laboratory Manual* (2nd ed., Cold Spring Harbor Laboratory Press, Cold Spring Harbor, N.Y. (1989) and Coligan et al. *Current Protocols in Immunology* (Current Protocols, Wiley Interscience (1994)), which are incorporated herein by reference. The nomenclatures utilized in connection with, and the laboratory procedures and techniques of, analytical chemistry, synthetic organic chemistry, molecular and cellular biology, and medicinal and pharmaceutical chemistry described herein are those well known and commonly used in the art. Standard techniques are used for chemical syntheses, chemical analyses, pharmaceutical preparation, formulation, and delivery, and treatment of patients.

All publications and patent applications mentioned in the specification are indicative of the level of skill of those skilled in the art to which the presently disclosed and claimed inventive concept(s) pertains. All publications and patent applications are herein incorporated The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of the presently disclosed and claimed inventive concept(s) have been described in terms of particular embodiments, it will be apparent to those of skill in the art that variations may be applied to the compositions and/or methods and in the steps or in the sequence of steps of the methods described herein without departing from the concept, spirit and scope of the inventive concept(s). All such similar substitutes and modifications apparent to those skilled in the art are deemed to be within the spirit, scope and concept of the inventive concept(s) as defined by the appended claims.

The presently disclosed and claimed inventive concept(s) is related to methods of treating cancer utilizing an enzyme prodrug therapy, as well as methods of producing cancer cell-targeted conjugates including the enzyme utilized in the enzyme prodrug therapy. The presently disclosed and claimed inventive concept(s) is further related to compositions comprising said conjugate and prodrug, wherein the compositions may be utilized in the methods of treating cancer described herein. The presently disclosed and claimed inventive concept(s) is also related to kits that include said conjugate and prodrug.

In another embodiment, the presently disclosed and claimed inventive concept(s) is also related to methods of treating cancer as described herein above, wherein such methods further include the use of an immunostimulant and/or chemotherapeutic agent in such methods. The presently disclosed and claimed inventive concept(s) also includes compositions that comprise the conjugate and prodrug as well as the immunostimulant and/or chemotherapeutic agent. In addition, the presently disclosed and claimed inventive concept(s) is also related to kits that include the conjugate, prodrug and immunostimulant and/or chemotherapeutic agent.

According to the presently disclosed and claimed inventive concept(s), conjugates for use in an enzyme prodrug cancer therapy treatment are provided. The presently disclosed and claimed inventive concept(s) provides conjugates that include a ligand having the ability to specifically and stably bind to an external receptor and/or binding site on an outer surface of a tumor vasculature endothelial cell and/or cancer cell, wherein the external receptor and/or binding site is specific for tumor vasculature endothelial cells and/or cancer cells (i.e., is uniquely expressed or overexpressed on a luminal surface of the tumor vasculature endothelial cell or cancer cell). In one embodiment, the conjugate is maintained on the outer surface of the tumor vasculature endothelial cell and/or cancer cell with substantially no internalization of the conjugate.

The conjugate further includes an enzyme that is operatively attached to the ligand, wherein the enzyme is able to convert a prodrug into an active anticancer drug.

The ligand of the conjugate of the presently disclosed and claimed inventive concept(s) may be any protein or composition which binds to the receptor or other targeting molecule uniquely present on the surface of cancer cells or cells in the tumor vasculature (i.e., an aminophospholipid). When the ligand is a protein, the ligand may contain the entire protein that binds to the desired receptor or other targeting molecule, or the ligand may contain only a portion of the protein. For example, it may be desirable to remove a portion of the protein that has an undesirable biological activity, or it may be desirable to remove a portion of the protein to enable attachment of the anticancer agent. The only requirement, when a portion of the protein is present as the ligand in the conjugate, is that the portion of the protein substantially retain the protein's receptor or targeting molecule binding activity. In addition, if the protein contains a portion that targets the protein for internalization, such portion should be removed so that the conjugate of the presently disclosed and claimed inventive concept(s) is stably bound to the outer surface of the cancer cell or blood vessel supplying the tumor. In one embodiment, the conjugate is maintained on the outer surface of the cancer cell or blood vessel with substantially no internalization thereof. The terms "portion" and "fragment" are used herein interchangeably.

Likewise, the conjugate may contain a variant of the ligand. For example, it may be desirable to modify a portion of the ligand that has an undesirable biological activity, or it may be desirable to modify a portion of the ligand to enable attachment of the anticancer agent. The only requirement, when a variant of the ligand is present in the conjugate, is that the ligand variant substantially retain the ligand's receptor or targeting molecule binding activity. Also, sequences may be added to, or inserted within, the ligand during modification, as long as the modified ligand substantially retains the ligand's receptor binding activity. Therefore, it is to be understood that the term "ligand variant" includes both substitutions (including but not limited to conservative and semi-conservative substitutions) as well as additions and insertions to the native ligand's sequence that do not substantially affect the ligand's receptor binding activity. Such variations may occur at the nucleic acid level during construction of the construct from which the conjugate is expressed, or the variations may be produced by other posttranscriptional or post-translational means known to those or ordinary skill in the art, including but not limited to, mutations and chemical modifications.

Examples of receptors that may be targeted by conjugates in accordance with the presently disclosed and claimed inventive concept(s) include urokinase receptor, epidermal growth factor (EGF) receptor, insulin-like growth factor receptor, interleukin-4 (IL-4) receptor, interleukin 6 (IL-6) receptor, keratinocyte growth factor (KGF) receptor, platelet-derived growth factor (PDGF) receptor, fibroblast growth factor (FGF) receptor, laminin receptor, vascular endothelial growth factor (VEGF) receptor, transferrin receptor, phosphatidylserine (PS), fibronectin, and the like, as well as portions thereof, and variants thereof, that substantially maintain the ability to bind to the ligand of the conjugate of the presently disclosed and claimed inventive concept(s) and/or maintain the conjugate on the surface of the cell with substantially no internalization thereof.

As stated above, the ligand portion of the conjugate specifically and stably binds to the external receptor or binding site on the outer surface of the cell. In one embodiment, the ligand may be selected from the group consisting of annexin V; antibodies to a receptor or aminophospholipid that is uniquely expressed or overexpressed on a surface of a tumor vasculature endothelial cell or cancer cell; RGD-motif peptides (Receptor: integrins alpha-v-beta 3 and alpha-v-beta 5); NGR-motif peptides (Receptor: aminopeptidase N, also known as CD13); F3, a 34-amino acid basic peptide from HMGN2 (Receptor: cell surface nucleolin); HWGF-motif peptides (selective inhibitors of matrix metalloproteinase-2 and matrix metalloproteinase-9, also known as gelatinase A and gelatinase B); the synthetic peptide CTTHWGFTLC (which targets angiogenic blood vessels, inhibits the migration of human endothelial cells and tumor cells, and also prevents tumor growth and invasion in animal models and improves survival of mice bearing human tumors; SEQ ID NO:9); amino-terminal fragment (ATF) of urokinase (which binds to the urokinase receptor, but, unlike full length urokinase, is not internalized); and fragments or variants thereof which substantially retain the ability to bind to the receptor or binding site. In one embodiment, the ligand may be a phosphatidylserine (PS)-binding protein.

Where used herein the term "annexin" refers to any of annexins 1-11 and 13, which are more particularly designated as annexins A1, A2, A3, A4, A5, A6, A7, A8, A9, A10, A11, and A13. Annexin V where used herein refers to Annexin A5, for example. The annexins contemplated herein further include non-human cognate orthologs of A1-A11 and A13 from non-human vertebrates, including but not limited to, non-human primates, dogs, cats, horses, livestock animals and zoo animals, which may be used for treatment in said non-human mammals in the methods contemplated herein. The annexins contemplated for use herein are discussed in further detail in V. Gerke and S. E. Moss (Physiol. Rev., 82:331-371 (2002)), the entirety of which is expressly incorporated by reference herein.

Anionic phospholipids are largely absent from the surfaces of resting mammalian cells under normal conditions. PS is the most abundant anionic phospholipid of the plasma membrane and is tightly segregated to the internal side of the plasma membrane in most cell types. Recently, it has been discovered that PS is expressed on the outside surface of the endothelial cells that line the blood vessels in tumors in mice but is not expressed on the outside surface of the vascular endothelium in normal organs. In addition, anionic phospholipids have been shown to be expressed on the outside surface of cancer cells.

The tumor vasculature is increasingly recognized as a target for cancer therapy. Angiogenesis, the formation of new capillaries from existing blood vessels, is essential for the growth of solid tumors beyond 1-3 mm in size. Damage to the endothelial cells that line the blood vessels results in the induction of the coagulation cascade, causing intratumoral vessel occlusion and subsequent tumor necrosis. Targeting the tumor vasculature has the advantage that the delivery vehicle, once in the bloodstream, has direct access to the target endothelial cells. Other advantages of targeting the tumor vasculature rather than the tumor cells themselves include a potentiation effect, because one blood vessel nourishes hundreds of tumor cells. There have, however, been no studies reported of targeting enzyme/prodrug therapy to the tumor vasculature.

Human annexin V, one protein contemplated for use herein, and which is a member of the annexin family of $Ca^{2+}$-dependent anionic phospholipid binding proteins (others are noted above), is operatively attached to or otherwise physically associated with an enzyme for targeting the tumor vasculature endothelial cells. Annexin V is a member of a class of widely distributed proteins which bind to anionic phospholipids and membranes in a $Ca^{2+}$-dependent manner. Annexin V is a monomeric protein, which has been crystallized and shown to consist of four tandem repeats of similar structure. Structural evidence shows that the N-terminus of annexin V is located at the surface of the protein and faces away from the membrane-binding side of the molecule. It was later found that the attachment of prourokinase at the N-terminus of annexin V did not alter its affinity for cell membranes in which PS was exposed on the membrane surface, which is consistent with the previous structural evidence.

Annexin V (and other annexins) binds with very high affinity to PS-containing phospholipid bilayers. Annexin V may be obtained as described in U.S. Pat. No. 7,393,833, issued to Lind et al. on Jul. 1, 2008, the entire contents of which are hereby expressly incorporated by reference.

Examples of other PS-binding proteins that can be used in substitution include those in the Annexin family (such as Annexin V), lactadherin, domains found in proteins known to bind PS, such as Factor V/Va, Factor X/Xa, Factor II/IIa, Factor VII/VIIa, Factor IX/IXa, Factor VIII/VIIIa, Spectrin, Class B Scavenger receptor type I, Protein Kinase C, and proteins containing the C2 domains of protein kinase C (this includes synaptotagmins), Rabphilin family members, the PS receptor, endothelial lectin-like OxLDL receptor-1 (LOX-1), antibodies to PS, phosphatidylserine decarboxylase, MARCKS (myristoylated, alanine-rich protein kinase C substrate), PS-p68, Myosin, Erythrocyte protein 4.1, hemoglobin, Calponin family members, S100A, S100B, calcyclin-binding protein family members, milk membrane-glycoprotein, MFG-E8 (milk fat globule-EGF factor 8), and other PS-binding motifs known to those of ordinary skill in the art.

Alternatively, the ligand of the conjugate of the present invention may be an anionic phospholipid-specific antibody, such as a phosphatidylserine specific monoclonal antibody, to which the anticancer agent is conjugated. Examples of PS specific monoclonal antibodies include those described in U.S. Pat. Nos. 6,312,694; 6,406,693; 6,783,760; 6,818,213;

and 7,067,109. The ligand to which the anticancer agent is associated may be a non PS binding moiety which binds to another tumor specific feature, such as those described in U.S. patent The modification of one of the receptor-binding ligands described herein above to provide a fragment or variant thereof that substantially maintains the receptor binding ability of the native receptor-binding ligand is fully within the skill of a person in the art and therefore is also within the scope of the presently disclosed and claimed inventive concept(s). The term "substantially maintains the receptor-binding ability of the native receptor-binding ligand" means that the protein fragment or variant maintains at least 50% of the native ligand's receptor-binding ability, and preferably, at least 75% of the native ligand's receptor-binding ability, and more preferably, at least 90% of the native ligand's receptor-binding ability.

The enzyme attached to the ligand may include any enzyme capable of converting a prodrug into an active anticancer drug that can function in accordance with the presently disclosed and claimed inventive concept(s). The enzyme should be of either nonhuman origin, or be a human protein that is absent or expressed only at low concentrations in normal tissues. Examples of enzymes that may be utilized in accordance with the presently disclosed and claimed inventive concept(s) include, but are not limited to, L-methioninase, nitroreductase, cytochrome P450, purine-nucleoside phosphorylase, thymidine kinase, alkaline phosphatase, β-glucuronidase, glycosidase, carboxypeptidase, carboxyesterase, penicillin amidase, β-lactamase, and cytosine deaminase. In one embodiment, the enzyme may be L-methioninase (also known as methionine γ-lyase).

In one embodiment, the enzyme may itself also have an anticancer activity. Examples of enzyme/anticancer agents that may be utilized in accordance with the presently disclosed and claimed inventive concept(s) include, but are not limited to, L-methioninase and fragments and variants thereof which substantially retain the ability to degrade methionine.

The enzyme and the ligand may be directly coupled together or indirectly coupled together via a linker. In addition, the enzyme may be conjugated to PEG, or the conjugate may be encapsulated in a liposome.

In one embodiment, the conjugate has an amino acid sequence comprising at least one of: (A) an amino acid sequence as set forth in at least one of SEQ ID NOS:2 and 4; (B) an amino acid sequence encoded by at least one of SEQ ID NOS:1 and 3; (C) an amino acid sequence that is at least 90% identical to at least one of SEQ ID NOS:2 and 4; (D) an amino acid sequence that is encoded by a nucleotide sequence that is at least 90% identical to at least one of SEQ ID NOS:1 and 3; (E) an amino acid sequence that differs from at least one of SEQ ID NOS:2 and 4 by less than 10 amino acids; (F) an amino acid sequence that differs from at least one of SEQ ID NOS:2 and 4 by less than 8 amino acids; (G) an amino acid sequence that differs from at least one of SEQ ID NOS:2 and 4 by less than 6 amino acids; and (H) an amino acid sequence that differs from at least one of SEQ ID NOS:2 and 4 by less than 5 amino acids.

The nucleotide sequence of SEQ ID NO:1 encodes the amino acid sequence of SEQ ID NO:2, whereas the nucleotide sequence of SEQ ID NO:3 encodes the amino acid sequence of SEQ ID NO:4. The two fusion proteins differ in that the nucleotide/amino acid sequences of the fusion protein of SEQ ID NOS:1/2 contain a single nucleic acid substitution when compared to the wild type annexin V sequence; this single nucleic acid substitution results in a single amino acid substitution in the amino acid sequence when compared to the wild type annexin V sequence. Specifically, a "tgc" codon (which encodes the amino acid cysteine) has been mutated to a "ttc" codon (which encodes the amino acid phenylalanine). This amino acid substitution occurs at amino acid 11 of Annexin V. However, the binding sites for the Annexin V protein involve amino acids 20-84, 91-156, 174-240, and 250-315, so this mutation is not significant. The nucleotide/amino acid sequences of SEQ ID NOS:3/4 contain the wild type Annexin V sequences.

The presently disclosed and claimed inventive concept(s) is also related to a purified nucleic acid segment encoding the conjugate described herein above, a recombinant vector comprising said nucleic acid segment, and a recombinant host cell comprising said recombinant vector.

The conjugate described herein above is utilized in combination with a prodrug. The prodrug utilized in accordance with the presently disclosed and claimed inventive concept(s) is a substrate for the enzyme of the conjugate and therefore is convertible into an active anticancer drug by the enzyme of the conjugate. For example but not by way of limitation, a doxorubicin prodrug is converted to doxorubicin by penicillin-V amidase, or a selenomethionine prodrug is converted to methylselenol by L-methioninase. Examples of other prodrugs that may be used in accordance with the presently disclosed and claimed inventive concept(s) include but are not limited to, methotrexate, 5-fluorouracil, daunomycin, adriamycin, and vinca alkaloid (Deonarain et al., Br. J. Cancer, 70:786-794 (1994). However, it is to be understood that the list above is not to be considered exhaustive, but rather that any prodrug known in the art or otherwise capable of functioning in accordance with the presently disclosed and claimed inventive concept(s) falls within the scope of the presently disclosed and claimed inventive concept(s).

Shown in Table 1 are examples of various enzyme prodrug combinations that may be utilized in accordance with the presently disclosed and claimed inventive concept(s). However, it is to be understood that the list in Table 1 is not to be considered exhaustive, but rather that any enzyme/prodrug combination known in the art or otherwise capable of functioning in accordance with the presently disclosed and claimed inventive concept(s) falls within the scope of the presently disclosed and claimed inventive concept(s).

The presently disclosed and claimed inventive concept(s) is also related to methods of treating a cancer tumor and/or cancer cells supplied by a tumor vasculature. In one embodiment, the method includes providing a conjugate as described herein above and providing a prodrug that is a substrate for the enzyme of the conjugate. In the method, the conjugate is administered to a patient in need thereof such that a therapeutically effective amount of the conjugate is brought into contact with at least one cancer cell and/or at least one blood vessel supplying a tumor. In one embodiment, the conjugate is maintained on the outer surface of the cancer cell and/or tumor vasculature endothelial cell with substantially no internalization thereof. The free conjugate not bound to the surface of the tumor cell and/or tumor vasculature is allowed to clear from the bloodstream, and then a therapeutically effective amount of the prodrug is administered to the patient. The prodrug comes into contact with the conjugate and is converted to an active anticancer drug by the enzyme, wherein a high local concentration of the active anticancer drug is generated in close proximity to the tumor cells and/or tumor vasculature. The active anticancer drug is then taken up by the tumor cell and/or tumor vasculature and is selectively toxic to the tumor cells and/or tumor vasculature. For example, the anticancer drug is carried across the artery wall to the tumor cells by diffusion and permeation flow (fluid permeates across the artery wall because the pressure is higher inside the artery than outside). Thus, the anticancer drug is released specifically in the tumor, which will cause cells in the tumor to die, including the tumor's endothelial cells that line the tumor vasculature. This will cause much less toxicity to normal organs and tissue compared to when the drug itself is injected into the bloodstream. Death of the tumor vasculature endothelial cells will lead to clotting of the tumor vasculature and cutting off of the blood supply of the tumor cells, thereby causing these cells to die.

TABLE 1

Examples of Enzyme Prodrug Systems

| Enzyme | Prodrug |
|---|---|
| Alkaline phosphatase | Etoposide phosphate |
| | Mitomycin C phosphate |
| | Doxorubicin phosphate |
| | Phenolmustard phosphate |
| Carboxypeptidase G2 | Benzoic mustard glutamates |
| | CMDA |
| Carboxypeptidase A | Methotrexate peptide |
| | Methotrexate alanine |
| Cytosine deaminase | 5-fluorocytosine |
| β-Lactamase | LY 266070 |
| | C-DOX |
| | PRODOX |
| | Cephalosporin mustards |
| | Cephalosporin-DACCP |
| | PROTAX |
| | Cephalosporin mitomycin C |
| | C-Mel |
| β-Glucoronidase | Phenol mustard glucuronide |
| | Daunorubicin glucuronide |
| | Glucuronide camptothecin |
| Nitroreductase | CB1954 |
| Penicillin amidase | N-(4'-hydroxyphenylacetyl) palytoxin |
| | Doxorubicin-phenoxyacetamide |
| | Melphalan-phenoxyacetamide |
| | N-(phenylacetyl) doxorubicin |
| | N-(phenylacetyl) melphalan |
| Carboxyesterases | CPT-11, Irinotecan |
| Glycosidases | Glycosides |
| Alcohol dehydrogenase | Alcohol |
| Cytochrome P450 | 4-Ipomeanol |
| | Ifosfamide |
| | Cyclophosphamide |
| Purine-nucleoside phosphorylase | Fludarabine |
| | MeP-dR |
| Methioinine γ-lyase | Selenomethionine |
| | Trifluoromethionine |
| Thymidine kinase | Ganciclovir |

Abbreviations
CMDA: 4-[N-(2-chloroethyl)-N-[2-(mesyloxy)ethyl]amino]benzoyl-L-glutamic acid
PROTAX: cephalothin-derived prodrug of taxol
C-Mel: cephalosporin carbamate derivative of melphalan
MeP-dR: 9-(β-2-deoxy-erythropentofuranosyl)-6-methylpurine In a particular embodiment of the methods of the presently disclosed and claimed inventive concept(s), the conjugate comprises a ligand bound to L-methioninase. The binding of the conjugate to the surface of the tumor cells and/or tumor vasculature results in a depletion of exogenous methionine in a vicinity of the cancer cell and/or tumor vasculature, whereby the conjugate itself is also selectively toxic to the cancer cells and/or tumor vasculature.

In an alternative embodiment of the presently disclosed and claimed inventive concept(s), the conjugate and prodrug compositions of the presently disclosed and claimed inventive concept(s) can be used with chemotherapeutic agents which have increased effectiveness at temperatures elevated above normal physiologic temperatures. Examples of chemotherapeutic agents which can be used herein include mitomycin C, nitrosureas, platin analogs, doxorubicin, mitoxantrone, alkylating agents, bleomycin, and anthracycline, thiotepa, cisplatin, methotrexate, cyclophosphamide, and amphotericin B. The cytotoxic drug produced by the conversion of the prodrug may also have increased effectiveness at elevated temperatures and may be used either by itself or in combination with another chemotherapeutic agent. The chemotherapeutic agents, the conjugate, and the prodrug compositions may be administered simultaneously, or the chemotherapeutic agent may be supplied after the conjugate and prodrug compositions have been administered and are ready to be irradiated. The simultaneous treatment with a cytotoxic drug and conjugate-prodrug heating therefore results in the increased killing of cancer cells as compared to when the cytotoxic drug is not administered with the conjugate-prodrug compositions. Dosages at which these chemotherapeutic agents are administered in thermochemotherapeutic treatments are known by those of ordinary skill in the art, for example as shown in Hahn et al. (Proc. Nt. Acad. Sci. 72:937-940 (1975)), Zee (Annals of Oncology, 13:1173-1184 (2002)), and Storm (Radiol. Clin. Nother Am. 27:621-627 (1989)).

In another embodiment of the presently disclosed and claimed inventive concept(s), the conjugate-prodrug compositions and methods of use thereof are combined with the use of an immunostimulant. The destruction of the tumor cells and/or tumor vasculature causes tumor antigens to be released into the bloodstream. Tumor antigens alone are not sufficient to stimulate an appropriate immune response (Dredge et al., Cancer Immunol. Immunother. 51:521-531 (2002). However, the addition of an immunostimulant has been shown to significantly enhance the immune response of the host to the tumor cells, which allows the immune system to mount a systemic attack on the remaining cells of the tumor.

Any immunostimulant known in the art or otherwise capable of functioning in accordance with the presently disclosed and claimed inventive concept(s) may be utilized in the compositions, methods and kits described herein. Examples of immunostimulants that may be utilized in accordance with the presently disclosed and claimed inventive concept(s) include, but are not limited to, glycated chitosan (Naylor et al., The British Journal of Dermatology, 155:1287-1292 (2006)); muramyldipeptide derivatives (Azuma et al., International Immunopharmacology, 1:1249-1259 (2001)); trehalose-dimycolates (Azuma et al., International Immunopharmacology, 1:1249-1259 (2001); BCG-cell wall skeleton (Azuma et al., International Immunopharmacology, 1:1249-1259 (2001)); various cytokines (Weiss et al., Expert opinion on biological therapy, 7:1705-1721 (2007)); and combinations and/or derivatives thereof. Dosages of immunostimulants can be in the range of 0.001 to 100 mg per kg of body weight per day, depending on the method of administration.

Therefore, the compositions of the presently disclosed and claimed inventive concept(s) may comprise at least one conjugate, at least one prodrug, and at least one immunostimulant (each as described herein above). Likewise, the kits of the presently disclosed and claimed inventive concept(s) may comprise at least one conjugate, at least one prodrug and/or at least one immunostimulant.

In the same manner, the methods described herein above may further include the step of administering an effective amount of an immunostimulant, wherein the immunostimulant is effective in significantly enhancing the immune response of the patient to the tumor cells, and thereby allowing the immune system to mount a systemic attack on the remaining cells of the tumor. The immunostimulant may be administered at the same time as either the conjugate or the prodrug, or may be administered before or after the administration of the conjugate and the prodrug; alternatively, the immunostimulant may be administered multiple times to the patient.

As utilized in accordance with the present disclosure, the following terms, unless otherwise indicated shall be understood to have the following meanings:

As used herein, the term "nucleic acid segment" and "DNA segment" are used interchangeably and refer to a DNA molecule which has been isolated free of total genomic DNA of a particular species. Therefore, a "purified" DNA or nucleic acid segment as used herein, refers to a DNA segment which contains a coding sequence isolated away from, or purified free from, unrelated genomic DNA, genes and other coding segments. Included within the term "DNA segment", are DNA segments and smaller fragments of such segments, and also recombinant vectors, including, for example, plasmids, cosmids, phage, viruses, and the like. In this respect, the term "gene" is used for simplicity to refer to a functional protein-, polypeptide-, or peptide-encoding unit. As will be understood by those in the art, this functional term includes genomic sequences, cDNA sequences or combinations thereof. "Isolated substantially away from other coding sequences" means that the gene of interest forms the significant part of the coding region of the DNA segment, and that the DNA segment does not contain other non-relevant large portions of naturally-occurring coding DNA, such as large chromosomal fragments or other functional genes or DNA coding regions. Of course, this refers to the DNA segment as originally isolated, and does not exclude genes or coding regions later added to, or intentionally left in, the segment by the hand of man.

In certain embodiments, DNA sequences in accordance with the presently disclosed and claimed inventive concept(s) will further include genetic control regions which allow the expression of the sequence in a selected recombinant host. The genetic control region may be native to the cell from which the gene was isolated, or may be native to the recombinant host cell, or may be an exogenous segment that is compatible with and recognized by the transcriptional machinery of the selected recombinant host cell. Of course, the nature of the control region employed will generally vary depending on the particular use (e.g., cloning host) envisioned.

Truncated genes also fall within the definition of preferred DNA sequences as set forth above. Those of ordinary skill in the art would appreciate that simple amino acid removal can be accomplished, and the truncated versions of the sequence simply have to be checked for the desired biological activity in order to determine if such a truncated sequence is still capable of functioning as required. In certain instances, it may be desired to truncate a gene encoding a protein to remove an undesired biological activity, as described herein.

Nucleic acid segments having a desired biological activity may be isolated by the methods described herein. The term "a sequence essentially as set forth in SEQ ID NO:X" means that the sequence substantially corresponds to a portion of SEQ ID NO:X and has relatively few amino acids or codons encoding amino acids which are not identical to, or a biologically functional equivalent of, the amino acids or codons encoding amino acids of SEQ ID NO:X. The term "biologically functional equivalent" is well understood in the art and is further defined in detail herein, as a gene having a sequence essentially as set forth in SEQ ID NO:X, and that is associated with the ability to perform a desired biological activity in vitro or in vivo.

The art is replete with examples of practitioner's ability to make structural changes to a nucleic acid segment (i.e., encoding conserved or semi-conserved amino acid substitutions) and still preserve its enzymatic or functional activity when expressed. See for special example of literature attesting to such: (1) Risler et al., "Amino Acid Substitutions in Structurally Related Proteins. A Pattern Recognition Approach." J. Mol. Biol. 204:1019-1029 (1988) [" . . . according to the observed exchangeability of amino acid side chains, only four groups could be delineated; (i) Ile and Val; (ii) Leu and Met, (iii) Lys, Arg, and Gln, and (iv) Tyr and Phe."]; (2) Niefind et al., "Amino Acid Similarity Coefficients for Protein Modeling and Sequence Alignment Derived from Main-Chain Folding Anoles." J. Mol. Biol. 219:481-497 (1991) [similarity parameters allow amino acid substitutions to be designed]; and (3) Overington et al., "Environment-Specific Amino Acid Substitution Tables: Tertiary Templates and Prediction of Protein Folds," Protein Science 1:216-226 (1992) ["Analysis of the pattern of observed substitutions as a function of local environment shows that there are distinct patterns . . . Compatible changes can be made"]

These references and countless others, indicate that one of ordinary skill in the art, given a nucleic acid sequence or an amino acid or an amino acid sequence, could make substitutions and changes to the nucleic acid sequence without changing its functionality. One of ordinary skill in the art, given the present specification, would be able to identify, isolate, create, and test DNA sequences and/or enzymes that produce natural or chimeric or hybrid molecules having a desired biological activity. As such, the presently claimed and disclosed inventive concept(s) should not be regarded as being solely limited to the specific sequences disclosed herein. Standardized and accepted functionally equivalent amino acid substitutions are presented in Table 2.

TABLE 2

| Amino Acid Group | Conservative and Semi-Conservative Substitutions |
|---|---|
| Nonpolar R Groups | Alanine, Valine, Leucine, Isoleucine, Proline, Methionine, Phenylalanine, Tryptophan |
| Polar, but uncharged, R Groups | Glycine, Serine, Threonine, Cysteine, Asparagine, Glutamine |
| Negatively Charged R Groups | Aspartic Acid, Glutamic Acid |
| Positively Charged R Groups | Lysine, Arginine, Histidine |

The DNA segments of the presently disclosed and claimed inventive concept(s) encompass DNA segments encoding biologically functional equivalent proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the enzyme activity or to antigenicity of the protein or to test mutants in order to examine biological activity at the molecular level or to produce mutants having changed or novel enzymatic activity and/or substrate specificity.

By "polypeptide" is meant a molecule comprising a series of amino acids linked through amide linkages along the alpha carbon backbone. Modifications of the peptide side chains may be present, along with glycosylations, hydroxylations and the like. Additionally, other nonpeptide molecules, including lipids and small molecule agents, may be attached to the polypeptide.

Another embodiment of the presently disclosed and claimed inventive concept(s) is a purified nucleic acid segment that encodes a protein in accordance with the presently disclosed and claimed inventive concept(s), further defined as being contained within a recombinant vector. As used herein, the term "recombinant vector" refers to a vector that has been modified to contain a nucleic acid segment that encodes a desired protein or fragment thereof. The recombinant vector may be further defined as an expression vector comprising a promoter operatively linked to said nucleic acid segment.

A further embodiment of the presently disclosed and claimed inventive concept(s) is a host cell, made recombinant with a recombinant vector comprising one or more genes encoding one or more desired proteins, such as a conjugate and/or a prodrug. The preferred recombinant host cell may be a prokaryotic cell. In another embodiment, the recombinant host cell is a eukaryotic cell. As used herein, the term "engineered" or "recombinant" cell is intended to refer to a cell into which one or more recombinant genes have been introduced mechanically or by the hand of man. Therefore, engineered cells are distinguishable from naturally occurring cells which do not contain a recombinantly introduced gene. Engineered cells are thus cells having a gene or genes introduced therein through the hand of man. Recombinantly introduced genes will either be in the form of a cDNA gene, a copy of a genomic gene, or will include genes positioned adjacent to a promoter associated, or not naturally associated, with the particular introduced gene.

In preferred embodiments, the DNA segments further include DNA sequences, known in the art functionally as origins of replication or "replicons", which allow replication of contiguous sequences by the particular host. Such origins allow the preparation of extrachromosomally localized and replicating chimeric or hybrid segments of plasmids, to which the desired DNA sequences are ligated. In more preferred instances, the employed origin is one capable of replication in bacterial hosts suitable for biotechnology applications. However, for more versatility of cloned DNA segments, it may be desirable to alternatively or even additionally employ origins recognized by other host systems whose use is contemplated (such as in a shuttle vector).

The nucleic acid segments of the presently disclosed and claimed inventive concept(s), regardless of the length of the coding sequence itself, may be combined with other DNA sequences, such as promoters, polyadenylation signals, additional restriction enzyme sites, multiple cloning sites, epitope tags, polyhistidine regions, other coding segments, and the like, such that their overall length may vary considerably. It is, therefore, contemplated that a nucleic acid fragment of almost any length may be employed, with the total length preferably being limited by the ease of preparation and use in the intended recombinant DNA protocol.

As used herein, a "conjugate" refers to a molecule that contains at least one receptor-binding ligand and at least one enzyme that are coupled directly or via a linker and that are produced by chemical coupling methods or by recombinant expression of chimeric DNA molecules to produce fusion proteins.

As used herein, the term "covalently coupled", "linked", "bonded", "joined", and the like, with reference to the ligand and enzyme components of the conjugates of the presently disclosed and claimed inventive concept(s), mean that the specified components are either directly covalently bonded to one another or indirectly covalently bonded to one another through an intervening moiety or components, such as a bridge, spacer, linker or the like. For example but not by way of limitation, the ligand and the enzyme may be chemically coupled together via a thioether linkage as described in Mickisch et al. (1993). Another example, but not by way of limitation, is the covalent linking of the ligand and the enzyme by a flexible peptide oligopeptide as described by Argos (*An investigation of oligopeptides linking domains in protein tertiary structures and possible candidates for general gene fusion*, J. Mol. Biol., 211, 943-958 (1990)).

The term "effective amount" refers to an amount of a biologically active molecule or conjugate or prodrug or derivative thereof sufficient to exhibit a detectable therapeutic effect without undue adverse side effects (such as toxicity, irritation and allergic response) commensurate with a reasonable benefit/risk ratio when used in the manner of the presently disclosed and claimed inventive concept(s). The therapeutic effect may include, for example but not by way of limitation, inhibiting the growth of undesired tissue or malignant cells. The effective amount for a subject will depend upon the type of subject, the subject's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

As used herein, the term "concurrent therapy" is used interchangeably with the terms "combination therapy" and "adjunct therapy", and will be understood to mean that the patient in need of treatment is treated or given another drug for the disease in conjunction with the conjugates of the presently disclosed and claimed inventive concept(s). This concurrent therapy can be sequential therapy where the patient is treated first with one drug and then the other, or the two drugs are given simultaneously.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism. A molecule can be biologically active through its own functionalities, or may be biologically active based on its ability to activate or inhibit molecules having their own biological activity.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

A "liposome" is a small vesicle composed of various types of lipids, phospholipids and/or surfactant. The components of the liposome are commonly arranged in a bilayer formation, similar to the lipid arrangement of biological membranes.

As used herein, the term "anticancer agent" refers to a molecule capable of inhibiting cancer cell function. The agent may inhibit proliferation or may be cytotoxic to cells. A variety of anticancer agents can be used and include those that inhibit protein synthesis and those that inhibit expression of certain genes essential for cellular growth or survival. Anticancer agents include those that result in cell death and those that inhibit cell growth, proliferation and/or differentiation. In one embodiment, the anticancer agent may be selectively toxic against certain types of cancer cells but does not affect or is less effective against other normal cells. For example but not by way of limitation, the anticancer agent may be a protein which degrades a nonessential amino acid wherein the nonessential amino acid is still required for growth of tumor cells, such as but not limited to, methioninase. In another embodiment, the anticancer agent is an antineoplastic agent.

The term "antineoplastic agent" is used herein to refer to agents that have the functional property of inhibiting a development or progression of a neoplasm in a human or animal, particularly a malignant (cancerous) lesion, such as a carcinoma, sarcoma, lymphoma, or leukemia. Inhibition of metastasis is frequently a property of antineoplastic agents.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer.

The term "patient" includes human and veterinary subjects. "Mammal" for purposes of treatment refers to any animal classified as a mammal, including human, domestic and farm animals, nonhuman primates, and any other animal that has mammary tissue.

The terms "treat", "treating" and "treatment", as used herein, will be understood to include both inhibition of tumor growth as well as induction of tumor cell death.

The term "receptor" as used herein will be understood to include any peptide, protein, glycoprotein, lipoprotein, polycarbohydrate, or lipid that is uniquely expressed or overexpressed on the surface of cancer cells or cells in the tumor vasculature and is exposed on the surface of cancer cells or cells in the tumor vasculature in a manner that will allow interaction with a circulating targeting agent, such as the conjugate.

The phrase "substantially no internalization", as used herein, refers to a lack of internalization of a substantial amount of the conjugates of the presently disclosed and claimed inventive concept(s). For example, the phrase "substantially no internalization" will be understood as less than 25% of the conjugates of the presently disclosed and claimed inventive concept(s) being internalized by a cell to which the conjugate is bound, or less than 10% of the conjugates of the presently disclosed and claimed inventive concept(s) being internalized by a cell to which the conjugate is bound, or less than 5% of the conjugates of the presently disclosed and claimed inventive concept(s) being internalized by a cell to which the conjugate is bound, or less than 3% of the conjugates of the presently disclosed and claimed inventive concept(s) being internalized by a cell to which the conjugate is bound, or less than 1% of the conjugates of the presently disclosed and claimed inventive concept(s) being internalized by a cell to which the conjugate is bound.

One example of an enzyme that may be utilized in accordance with the presently disclosed and claimed inventive concept(s) is L-methioninase. The relative reactivity of L-methioninase from P. putida for the DL-selenomethionine substrate is 2.8 times that for the L-methionine substrate (Esaki, N. and Soda, K., 1987, L-methionine γ-lyase from Pseudomonas putida and Aeromonas, Methods in Enzymology, 143, 459-465). In addition, L-methioninase also functions as an anticancer agent. Cancer cells of all types have an elevated requirement for methionine compared to normal cells, and all exogenous methionine in the vicinity of the cancer cells will be substantially depleted with L-methioninase bound to the cell surface in accordance with the presently disclosed and claimed inventive concept(s). The use of L-methioninase as an antitumor reagent in anti-methionine chemotherapy has been well documented and is described in detail in U.S. Pat. No. 5,690,929, issued to Lishko et al. on Nov. 25, 1997; U.S. Pat. No. 5,888,506, issued to Tan on Mar. 30, 1999; and U.S. Pat. No. 6,231,854, issued to Yuying on May 15, 2001, the contents of each of which are hereby expressly incorporated herein by reference in their entirety.

Purified L-methioninase from any source may be utilized in accordance with the presently disclosed and claimed inventive concept(s). Optionally, recombinant L-methioninase expressed from any genes known in the art or later identified that have common activity and/or sequence identity with currently known L-methioninase sequences may be utilized in accordance with the presently disclosed and claimed inventive concept(s). Further, the L-methioninase utilized in accordance with the presently disclosed and claimed inventive concept(s) may be truncated or modified to contain substitutions or insertions when compared with known L-methioninase sequences. The truncation or modification of L-methioninase sequences to provide a protein which substantially retains the ability to degrade methionine is fully within the skill of a person in the art and therefore is also within the scope of the presently disclosed and claimed inventive concept(s).

The gene for L-methioninase from P. putida has been cloned by two different research groups (Hori et al., Cancer Res., 56:2116-2122 (1996), and Inoue et al., J Biochem (Tokyo), 117:1120-1125 (1995)). The genes for two L-methioninases from the primitive protozoan parasite Trichomonas vaginalis have been cloned, and the two L-methioninases have been expressed in E. coli as a fusion with a six-histidine tag and were purified (McKie et al., J Biol. Chem., 273:5549-5556 (1998). The six-hisitidine tag was at the N-terminus for one of the L-methioninases and at the C-terminus for the other. Both of these recombinant fusion proteins produced very high methioninase activity.

Since the enzymes described herein are typically bacterially-derived proteins, the enzymes of the conjugate of the presently disclosed and claimed inventive concept(s) may be modified so as to reduce the immunogenicity thereof. One method for reducing a protein's immunogenicity is to conjugate the protein to polyethylene glycol (PEG). For example but not by way of limitation, L-methioninase has been successfully conjugated to PEG, resulting in a 36-fold increase in serum half-life and the elimination of immunogenic reactions while maintaining the same antitumor efficacy in vitro as the unmodified L-methioninase (Yang et al., 2004). In guinea pigs, there was no detectable immune response after L-methioninase conjugated to PEG was injected, while shock and death resulted when unmodified L-methioninase was injected.

By "polyethylene glycol" or "PEG" is also meant any other polyalkylene glycol compound or a derivative thereof, with or without coupling agents or derivatization with coupling or activating moeities (e.g., with thiol, triflate, tresylate, azirdine, oxirane, or preferably with a maleimide moiety). Compounds such as maleimido monomethoxy PEG are exemplary or activated PEG compounds of the presently disclosed and claimed inventive concept(s). Other polyalkylene glycol compounds, such as polypropylene glycol, may be used in the presently disclosed and claimed inventive concept(s). Other appropriate polymer conjugates include, but are not limited to, non-polypeptide polymers, charged or neutral polymers of the following types: dextran, colominic acids or other carbohydrate based polymers, biotin deriviatives and dendrimers, for example. The term PEG is also meant to include other polymers of the class polyalkylene oxides.

The PEG can be linked to any N-terminal amino acid of the conjugate, and/or can be linked to an amino acid residue downstream of the N-terminal amino acid, such as lysine, histidine, tryptophan, aspartic acid, glutamic acid, and cysteine, for example or other such linkable amino acids known to those of skill in the art. Cysteine-pegylated conjugates, for example, are created by attaching polyethylene glycol to a thio group on a cysteine residue of the conjugate.

The PEG moiety attached to the conjugate may range in molecular weight, for example, from about 200 to 40,000 MW.

The conjugates contemplated herein can be adsorbed or linked to PEG molecules using techniques shown, for example (but not limited to), in U.S. Pat. Nos.: 4,179,337; 5,382,657; 5,972,885; 6,177,087; 6,165,509; 5,766,897; and 6,217,869; and Published Application 2006/0275371; the specifications and drawings each of which are hereby expressly incorporated by reference herein in their entirety.

Thus, the above-described studies demonstrate that the immunological response to the enzyme can be greatly reduced or eliminated by either conjugation to PEG or by encapsulation in liposomes, without significant effect on enzymatic activity of the enzyme. Liposome encapsulation has the advantage that covalent attachment of moieties to the enzyme is not required, which may be helpful to preserve binding of the proposed conjugates to the receptors on cancer cells.

The compositions of the presently disclosed and claimed inventive concept(s) (including the conjugates, prodrugs, immunostimulants and/or chemotherapeutic agents described herein) may be administered to a subject by any methods known in the art, including but not limited to, oral, topical, transdermal, parenteral, subcutaneous, intranasal, intramuscular, intraperitoneal, and intravenous routes, including both local and systemic applications. In addition, the compositions of the presently disclosed and claimed inventive concept(s) may be designed to provide delayed or controlled release using formulation techniques which are well known in the art.

The presently disclosed and claimed inventive concept(s) also includes a pharmaceutical composition comprising a therapeutically effective amount of any of the compositions described herein above in combination with a pharmaceutically acceptable carrier. As used herein, a "pharmaceutically acceptable carrier" is a pharmaceutically acceptable solvent, suspending agent or vehicle for delivering the conjugates of the presently disclosed and claimed inventive concept(s) to the human or animal. The carrier may be liquid or solid and is selected with the planned manner of administration in mind. Examples of pharmaceutically acceptable carriers that may be utilized in accordance with the presently disclosed and claimed inventive concept(s) include, but are not limited to, PEG, liposomes, ethanol, DMSO, aqueous buffers, oils, and combinations thereof.

EXAMPLE

The following example serves to illustrate certain useful embodiments and aspects of the presently disclosed and claimed inventive concept(s) and is not to be construed as limiting the scope thereof. Alternative materials and methods can be utilized to obtain similar results.

The objective of this Example was to develop a novel enzyme prodrug therapy for cancer that specifically targets the tumor vasculature and cancer cells even if the cancer cells metastasize to other parts in the body. The methods of the presently disclosed and claimed inventive concept(s) comprise the step of constructing a fusion protein (FP) composed of the annexin V protein and an enzyme that will convert a nontoxic prodrug into an anticancer prodrug. The annexin V portion of the FP targets the FP to tumors and their vasculature.

The use of L-methioninase as the enzyme portion of the L-methioninase-annexin V (Meth-AnnV) fusion protein acts in two ways. First, it catalyzes the conversion of the non-toxic prodrug selenomethionine (SeMet) into the drug methylselenol which, by means of permeation and diffusion, travels inside the cells and causes their death (FIG. 1). Second, it cuts off the methionine supply to the cancer cells by degrading it and depleting it from the vicinity of the tumors. The death of the endothelial cells causes the clotting of tumor vasculature, preventing cancer cells from getting necessary nutrients and oxygen. The breaking up of the cells also causes the release of tumor antigens in the blood stream, leading the immune system to mount an attack against tumors throughout the body. Even though the FP is relatively large (316 kDa), the large gaps that characterize the tumor vasculature will allow the Meth-AnnV FP to be transported through and bind to the cancer cells.

Such a therapy has many advantages. First, the FP is relatively easy to produce and purify. Second, the FP can be easily administered through an intravenous injection. Third, there are minimal side effects since the drug is generated locally in the tumor. Fourth, metastasizing cells anywhere in the body are targeted by the FP. Fifth, the breaking up of the endothelial cells causes the release of tumor antigens into the bloodstream, leading the immune system to mount an immune attack against cancer cells throughout the body. Sixth, said therapy utilizes a combination of two mechanisms to fight the cancer cells (i.e., deplete methionine and convert the prodrug into a drug).

The L-methionine portion of the FP is from bacteria and could potentially cause an immune response. One effective way to reduce a protein's immunogenicity is to conjugate it to polyethylene glycol (PEG) (Abuchowski et al., 1977). In fact, L-methioninase has been conjugated to PEG, and the administration of PEG-L-methioninase to monkeys has been shown to eliminate anaphylactic reactions (Yang et al., 2004).

Materials & Methods of the Example

Materials: Oligonucleotide primers were synthetically produced by the Molecular Biology Resource Facility at the Health Sciences Center of the University of Oklahoma. Linear pET-30 Ek/LIC vector, T4 DNA polymerase, HRV 3C protease, NovaBlue and BL21(DE3) *E. coli* cells were obtained from Novagen (Madison, Wis.). Bam HI restriction enzyme and T4 DNA ligase were purchased from New England Biolabs (Ipswich, Mass.). Cell culture media were obtained from ATCC (Manassas, Va.). Streptavidin-HRP was purchased from KPL (Gaithersburg, Md.). PCR and plasmid purification kits were from Qiagen (Vista, Calif.). Alamar Blue solution was obtained from Sigma-Aldrich (St. Louis, Mo.).

Construction of Recombinant Expression Plasmid: A gene for a fusion protein (FIG. 2), coding for L-methionine-α-deamino-γ-mercaptomethane-lyase (or L-methioninase) from *Pseudomonas putida* linked to human annexin V, was cloned into *E. coli* on the vector pET-30 Ek/LIC, which incorporates a $His_6$ tag at the N-terminus and an HRV 3C protease site just before the start of the desired protein. L-methioninase and annexin V are connected by a flexible linker consisting of amino acid residues 400-405 of SEQ ID NO:2 in the methioninase-annexin V (Meth-AnnV) fusion protein. The nucleotide sequence encoding the methioninase-annexin V fusion protein is set forth in SEQ ID NO:1, while the amino acid sequence of the Meth-AnnV fusion protein is set forth in SEQ ID NO:2.

The expression vector pET-30 Ek/LIC/METHANX, encoding the methioninase-annexin V fusion protein (FP), was constructed in the following manner: The DNA sequences encoding for the FP were amplified from pKK223-3/ATF-Meth (Zang et al., 2006) and pET-22b(+)/STFANX (obtained from Dr. Stuart Lind at the University of Oklahoma Health Sciences Center) by the polymerase chain reaction using the Expand High Fidelity PCR system (Boehringer Mannheim, Indianapolis, Ind.). The primers used for PCR to create the fusion protein gene were as follows:

```
(a) 5' primer for L-methioninase:
                                  (SEQ ID NO: 5)
5'- GAC/ GAC/ GAC/ AAG/ ATG/ CTT/ GAA/ GTC/ CTC/

TTT/ CAG/ GGA/ CCC/ CGC/ GAC/ TCC/ CAT/ ACC/ AAC/

ACC -3';

(b) 3' primer for L-methioninase:
                                  (SEQ ID NO: 6)
5'- GC/ CGC/ ATT/ GGA/ TCC/ AGA/ ACC/ GCT/ GCC/

TGC/ ACA/ CGC/ CTC/ CAA/ CGC/ CAA/ CTC/ G -3';

(c) 5' primer for annexin V:
                                  (SEQ ID NO: 7)
5'- CG/ ATT/ CGC/ GGA/ TCC/ GCA/ CAG/ GTT/ CTC/

AGA/ GGC -3';
and (d) 3' primer for annexin V:
                                  (SEQ ID NO: 8)
5'- GA/ GGA/ GAA/ GCC/ CGG/ TTA/ GTC/ ATC/ TTC/

TCC/ ACA/ GAG/ C -3'.
```

The L-methioninase primers incorporated a 5' LIC cloning site (italics), an HRV 3C protease site (bold), and a 3' BamHI site (underlined). The annexin V primers added a 5' BamHI site (underlined) and a 3' LIC cloning site (italics).

The PCR products were purified using the QIAquick PCR purification kit, digested with BamHI restriction enzyme, and purified with this same kit. The pure, digested genes were then ligated using T4 DNA ligase and run on an agarose gel. Using the QIAquick gel purification kit, the proper fragments were cut from the gel and purified. The pure methioninase-annexin V fusion gene was annealed to the pET-30 Ek/LIC linear vector using T4 DNA polymerase to create sticky ends and was transformed into competent NovaBlue cells. After successful transformation, plasmids containing the proper fusion gene insert were extracted from the NovaBlue cells using the QIAprep plasmid purification protocol and transformed into *E. coli* BL21(DE3) to be used as the host for protein expression. The final vector contains integrated thrombin and enterokinase cleavage sites, an N-terminal His-tag sequence for easy purification, and an engineered HRV 3C protease cleavage site that cleaves the sequence LEVLFQ↓GP at the start of the methioninase-annexin V gene. Sequencing of the FP gene was performed by the Oklahoma Medical Research Foundation (Oklahoma City, Okla.).

Expression and Purification of Recombinant Protein: Recombinant Meth-AnnV fusion protein was produced and purified by methods similar to those used by Zang et al. (2006). A culture of *E. coli* BL21(DE3) harboring pET-30 Ek/LIC with the fusion gene was grown in 10 ml of LB medium containing 35 µg/ml kanamycin overnight at 37° C. with shaking. This cell culture was added to 1 liter of fresh culture medium, and the culture was grown with shaking at 37° C. This cell culture was grown to mid-log phase ($OD_{600}$=0.5), and protein expression was induced by adding isopropyl β-D-thiogalactopyranoside (IPTG) to a final concentration of 0.4 mM. After addition of IPTG, the shaking of cell culture was continued at 30° C. for 5 hours and harvested by centrifugation for 10 minutes at 1000×g. The cell pellet was resuspended in 40 ml of sonication buffer containing 0.05 mM N— p-tosyl-L-phenylalanine chloromethyl ketone (TPCK), 1 mM phenylmethylsulfonyl fluoride (PMSF), 1% ethanol, 0.02 mM pyridoxal phosphate, 0.01% β-mercaptoethanol and 0.02 M sodium phosphate at pH 7.4. The cells were lysed by sonication at 4° C. for 30 seconds at 4.5 watts per ml of lysate and then allowed to cool for 30 seconds on ice. This cycle was repeated for four times for a total sonication time of 2.5 minutes. The lysate obtained was centrifuged at 12,000×g for 30 minutes to remove the cell debris.

All the purification steps were performed at 4° C. The entire purification procedure, outlined in FIG. 3, was performed as follows: Imidazole (30 mM) and NaCl (500 mM) were added to the lysate to reduce non-specific protein binding. This resulting mixture was fed to 5 ml HisTrap chromatography column, which was equilibrated with wash buffer containing 20 mM sodium phosphate, 30 mM imidazole, 500 mM NaCl, 0.02 mM pyridoxal phosphate at pH 7.4. The column was washed with the wash buffer to remove unwanted proteins. His-tagged fusion protein was eluted using elution buffer containing 20 mM sodium phosphate, 500 mM imidazole, 500 mM NaCl, 0.02 mM pyridoxal phosphate at pH 7.4. Eluted protein was dialyzed overnight against buffer containing 20 mM sodium phosphate and 0.02 mM pyridoxal phosphate at pH 7.4 to remove NaCl and imidazole from the protein solution and make suitable for N-terminal His-tag cleavage. The cleavage of N-terminal His-tag was achieved by using HRV 3C protease. HRV 3C protease (10 Units/mg of protein) and recommended 10× buffer (1.5 M NaCl, 0.5 M Tris-HCl, pH 7.5) were added to the protein solution. This reaction was carried out for 16 hours at 4° C.

Imidazole (30 mM) and NaCl (500 mM) were added to the cleaved protein solution, which was fed again onto a 5 ml HisTrap column. Purified protein was collected in the flowthrough from the column. Purified protein was dialyzed overnight against 20 mM sodium phosphate buffer at pH 7.4 containing 0.02 mM pyridoxal phosphate and 0.1 M NaCl. This formulation was flash-frozen using liquid nitrogen and then lyophilized in tubes at a concentration of 1-2 mg/ml.

Protein Content and Enzymatic Activity Determination: The Bradford assay from Bio-Rad (Hercules, Calif.) was used for all protein determinations throughout the purification using bovine serum albumin (BSA) as the standard. Samples were analyzed by denaturing gel electrophoresis using the SDS-PAGE method with Coomassie blue staining (Laemmli, 1970). The L-methioninase enzyme activity was measured using L-methionine as a substrate by the spectrophotometric determination of α-ketobutyrate with 3-methyl-2-benzothiazolone hydrazone hydrochloride (Esaki et al., 1987).

Cell Culture: Human HAAE-1 aorta endothelial cells were grown in F-12K medium with 2 mM L-glutamine and 1.5 g/L sodium bicarbonate and supplemented with 10% fetal bovine serum (FBS), 0.03 mg/ml endothelial cell growth supplement, and 0.1 mg/ml heparin. MCF-7 human breast cancer cells were maintained as monolayer cultures in Eagle's Minimum Essential medium supplemented with 10% FBS and 0.01 mg/ml bovine insulin. MDA-MB-231 human breast cancer cells were grown in Leibovitz's L-15 medium supplemented with 10% FBS. Penicillin-streptomycin solution at 10 µl/ml was also added to each medium (gives 100 units/ml for penicillin and 100 µg/ml for streptomycin). HAAE-1 and MCF-7 cells were grown at 37° C. in a 5% $CO_2$ atmosphere, while MDA-MB-231 cells were grown without $CO_2$ at 37° C.

Fusion Protein Binding Assay: Endothelial cells were grown to 70-80% confluence in T-75 flasks. Cells were transferred to 24-well culture plates ($5 \times 10^4$ cells/well) and grown to 80-85% confluence. Cells were fixed to the plate using 0.25% glutaraldehyde in binding buffer (PBS with 2 mM $Ca^{2+}$). Excess aldehyde groups were quenched using 50 mM $NH_4Cl$ in binding buffer. Varying concentrations of biotinylated FP were diluted in binding buffer containing 0.5% BSA and incubated at 37° C. for 2 hours. After washing with binding buffer with 0.5% BSA, streptavidin-HRP was added at 2 µg/ml and incubated at room temperature for 1 hour. Following washing with binding buffer, HRP was measured by adding the chromogenic substrate O-phenylenediamine (0.4 mg/ml) and hydrogen peroxide (0.012%) in phosphate-citrate buffer. After 30 minutes at room temperature in the dark, the solution was transferred to a transparent 96-well plate, and the absorbance was read at 450 nm on a microtiter plate reader. All experiments had a blank that was subjected to the same procedure but with no FP added. To determine non-specific binding, the same procedure was performed with no $Ca^{2+}$ and 5 mM EDTA in the binding buffer. The FP was biotinylated using SureLINK Chromophore Biotin (Gaithersburg, Md.) using a 40 molar excess of biotin.

Binding Stability Assay: To assess how long the FP remains bound to the surface of the endothelial cells, a modified binding assay was used. Cells on 24-well plates were first incubated for 2 hours at 37° C. in a saturating concentration of biotinylated FP (50 nM) in complete growth medium with 2 mM $Ca^{2+}$. Then, the cells were fixed either at day 0, 1, 2 or 3 with 0.25% glutaraldehyde in binding buffer. Excess aldehyde groups were quenched by incubation in a 50 mM $NH_4Cl$ in binding buffer. The binding of FP was then quantitated using the same procedure used in the FP binding assay (see above).

In Vitro Enyzme Prodrug Cytotoxicty to Cells: The experiment lasted 3 days, using the same cells for each of the days (day 0, 1, 2, and 3). Cells were grown and plated in 24-well plates with respective growth media using the same procedure as for the FP binding assay (see above). Each medium was supplemented with 2 mM $Ca^{2+}$ and 0.02 mM pyridoxal phosphate (since annexin V is $Ca^{2+}$ dependent and pyridoxal phosphate is a cofactor for L-methioninase). On day 0, a saturating concentration of FP was diluted in medium was added and incubated for 2 hours at 37° C. The plates were washed, and medium containing SeMet varying from 0 to 500 µM was added. The Alamar Blue assay was performed on all wells on day 0. The Alamar Blue assay was performed by adding Alamar Blue solution to each well to give 10% Alamar Blue and then incubating for 4 hours at 37° C. The solution was transferred to an opaque 96-well plate, and the fluorescence was read at 590 nm using excitation at 530 nm. The blank consisted of wells containing only medium (no cells). After the fluorescence reading, the plates were washed, replaced with fresh medium, and then placed in incubator. The readings were taken every 24 hours for the duration of the experiment.

Data Analysis: All assays included wells in triplicate. To test differences in cell viability, a two-tailed T-test was used. Group differences resulting in p values of less than 0.05 were considered to be statistically significant, p values of less than 0.01 were considered to be very significant, and p values of less than 0.001 were considered to be extremely significant.

Results of the Example

Protein Purification: The specific activity and recovery of the FP during the purification process are shown in Table 3. The yield of purified FP was 30 mg from 1 liter of culture medium. An SDS-PAGE gel image showing the purified proteins methioninase-annexin V, L-methioninase, and annexin V is shown in FIG. 4. (L-methioninase and annexin V were expressed and purified using essentially the same methods as for methioninase-annexin V). It can be seen in FIG. 4 that the three proteins are substantially pure. The lyophilized FP was determined to have a methioninase specific activity of 1.0 U/mg of protein. The overall recovery yield of L-methioninase activity was found to be 26%. L-methioninase activity remained relatively constant when stored in lyophilized form at −80° C.

TABLE 3

Specific activities and recovery yields during the Meth-AnnV purification steps.

| Step | Volume (mL) | Protein concentration (mg/mL) | Total amount of protein (mg) | Activity in sample (U/mL) | Total units | Specific activity (U/mg) | Recovery Yield (%) |
|---|---|---|---|---|---|---|---|
| Sonication supernatant | 40 | 7.19 | 287.60 | 2.13 | 85.20 | 0.30 | 100% |
| Chromatography 1 flow-through | 60 | 3.90 | 234.00 | 0.08 | 4.80 | 0.02 | 6% |
| Chromatography 1 elution | 16 | 3.30 | 52.80 | 3.55 | 56.80 | 1.08 | 67% |
| After 1$^{st}$ dialysis | 17 | 3.12 | 53.04 | 2.52 | 42.84 | 0.81 | 50% |
| After cleavage | 19 | 2.82 | 53.58 | 2.28 | 43.32 | 0.81 | 51% |
| Chromatography 2 flow-through | 29 | 0.78 | 22.74 | 1.68 | 48.72 | 2.14 | 57% |
| Chromatography 2 | 10.5 | — | — | 0.08 | 0.84 | — |

TABLE 3-continued

Specific activities and recovery yields during the Meth-AnnV purification steps.

| Step | Volume (mL) | Protein concentration (mg/mL) | Total amount of protein (mg) | Activity in sample (U/mL) | Total units | Specific activity (U/mg) | Recovery Yield (%) |
|---|---|---|---|---|---|---|---|
| elution |  |  |  |  |  |  |  |
| After 2$^{nd}$ dialysis | 28 | 0.87 | 24.36 | 0.65 | 18.20 | 0.75 | 21% |
| After filtration | 28 | 0.76 | 21.28 | 0.69 | 19.32 | 0.91 | 23% |
| After lyophilized | 28 | 0.76 | 21.28 | 0.79 | 22.12 | 1.04 | 26% |

Binding of Fusion Protein: The ability of the Meth-AnnV FP to bind to human endothelial cells and breast cancer cells with PS exposed on the cell surface was evaluated by equilibrium binding experiments in which increasing concentrations of biotin-labeled FP were used. In initial experiments with endothelial cells, hydrogen peroxide was used at a low concentration (1 mM) to induce exposure of PS. In later experiments, the $H_2O_2$ was omitted with little change in the results; therefore, the data reported here is with no $H_2O_2$ added. No $H_2O_2$ was added in the experiments with the breast cancer lines, since it has been reported that cancer cells express PS when grown in vitro (Sugimura et al., 1994; and Utsugi et al., 1991).

A typical equilibrium binding result for endothelial cells is shown in FIG. 5. The non-specific binding, obtained in the absence of $Ca^{2+}$, is subtracted from the total binding to obtain the specific binding. The dissociation constant ($K_d$) for each cell line tested was obtained from the specific binding data using Prism 5 software (GraphPad Software, San Diego, Calif.) to give the following results: 1.7±0.6 nM for endothelial cells, 1.9±1.2 nM for MCF-7 breast cancer cells, and 2.2±1.2 nM for MDA-MB-231 breast cancer cells. These results indicate that the binding of the FP to these cells is relatively strong. Literature values of annexin V binding alone to endothelial cells have been reported from 2.7-15.5 nM (van Heerde et al., 1994a and b). Thus, the $K_d$ values that have been measured herein are lower than those reported in the literature for annexin V alone, indicating that the binding of the fusion protein is stronger; this is probably because the FP exists as a tetramer, giving four annexin V molecules able to bind per FP molecule.

Binding Stability: To assess how long the FP remains bound to the surface of the endothelial cells, a modified binding assay was used. Cells on 24-well plates were first incubated for 2 hours at 37° C. in a saturating concentration of biotinylated FP (50 nM) in complete growth medium with 2 mM $Ca^{2+}$. Increased amounts of L-methionine were added to offset the methionine depletion effect (500 μM for endothelial cells and MDA-MB-231 cells, and 2000 μM for MCF-7 cells). Then, the cells were fixed either at day 0, 1, 2 or 3 with 0.25% glutaraldehyde in binding buffer. Excess aldehyde groups were quenched by incubation in a 50 mM $NH_4Cl$ in binding buffer. The binding of FP was then quantified using the same procedure used in the equilibrium FP binding assay. The stability of FP binding for 3 days was normalized by the viability of the cells, as shown in FIG. 6 for the three cell lines. Cell viability, as measured by the Alamar Blue assay, was found to be linearly proportional to the number of cells (data not shown). The data in FIG. 6 indicate a steady decline in FP bound over 3 days, but there is still some FP bound at day 3. For each cell line, the slope by linear regression of the absorbance/RFU versus time data was obtained, with results as follows: $3.07 \times 10^{-5}$ per day for the endothelial cells (HAAE-1), $4.63 \times 10^{-5}$ per day for the MCF-7 cells, and $5.38 \times 10^{-5}$ per day for the MDA-MB-231 cells. Thus, the rate of change of absorbance/RFU was the lowest for the endothelial cells.

Test of the anticancer activity in vitro of the L-methioninase-annexin V fusion protein in combination with selenomethionine prodrug on endothelial cells and breast tumor cells: The ability of the enzyme prodrug system to eliminate human endothelial cells and breast cancer cells was evaluated using cells grown in vitro and plated on 24-well plates. A saturating concentration of FP was added, followed by concentrations of SeMet ranging from 0 to 500 μM. Hydrogen peroxide was not used in the tests with endothelial cells because of the previous finding in the binding studies that deletion of hydrogen peroxide did not affect the binding results. For each cell line, the methionine concentration in the medium was set at a level that would not lead to a significant decrease in cell viability because of methionine depletion with FP present. Each of the cell lines in question metabolized the Alamar Blue to produce a fluorescence that was measured to quantify total cell viability. For each day, the fluorescence data from the Alamar Blue assay was expressed as a percentage of the fluorescence for the cells with no FP and 0 μM SeMet (control). Cells with no FP that were treated with different SeMet concentrations were compared to the control for each day, whereas cells that had the FP were compared to cells with the same SeMet concentration but no FP for each day.

The results for endothelial cells in medium that contained 500 μM L-methionine are shown in FIG. 7. Significant cell killing was found at days 2 and 3 for 10 and 100 μM SeMet (at day 2, $p<0.05$; at day 3, $p<0.05$ for 10 μM SeMet and $p<0.01$ for 100 μM SeMet). For MCF-7 breast cancer cells containing 2000 μM L-methionine, there was significant cell killing at day 2 with 500 μM SeMet and at day 3 with 100 and 500 μM SeMet (FIG. 8, $p<0.01$). At day 3 with no FP and 500 μM SeMet, cell viability was significantly lower ($p<0.05$), indicating that SeMet by itself is somewhat toxic to cells. FIG. 9 shows the results for MDA-MB-231 breast cancer cells with 500 μM L-methionine. With no SeMet present, there was a significant decrease in cell viability when the FP was added, indicating that the L-methionine level needs to be higher. However, there was significant killing of MDA-MB-231 cells for 10 and 500 μM SeMet at days 1, 2 and 3 (at day 1, $p<0.05$ for 10 and 500 μM SeMet; at day 2, $p<0.001$ for 10 and 500 μM SeMet; and at day 3, $p<0.001$ for 10 μM SeMet and $p<0.01$ for 500 μM SeMet).

Discussion of the Example

In this Example, it has been shown that the Meth-AnnV fusion protein developed for use in a new enzyme prodrug system binds strongly to the surface of endothelial cells and two breast cancer cell lines with similar $K_d$ values. The fact that the $K_d$ values are lower than those reported in the literature for annexin V alone, indicating stronger binding, is probably because there are four annexin V molecules per FP molecule.

The binding stability data show a steady decline in FP on the surface of all three cell types over a period of 3 days. For the endothelial cells, the data indicate that additional fusion protein will need to be added at 3 days for the enzyme prodrug effect to continue to be effective in the tumor vasculature. The results of enzyme prodrug treatment show that the killing of all three cell types is related to the dose of SeMet prodrug; the data also show that the cell killing increases with time until near complete killing in some cases.

Thus, in accordance with the presently disclosed and claimed inventive concept(s), there have been provided conjugate and prodrug compositions, as well as kits containing same and methods of producing and utilizing same that fully satisfy the objectives and advantages set forth hereinabove. Although the presently disclosed and claimed inventive concept(s) has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the presently disclosed and claimed inventive concept(s).

REFERENCES

The following references, to the extent that they provide exemplary procedural or other details supplementary to those set forth herein, are specifically incorporated herein by reference.

Abuchowski, A., van Es, T., Palczuk, N. C., and Davis, F. F. (1977). Alteration of immunological properties of bovine serum albumin by covalent attachment of polyethylene glycol. J Biol Chem 252, 3578.

Bagshawe, K. D. (2006). Antibody-directed enzyme prodrug therapy (ADEPT) for cancer. Expert Rev Anticancer Ther 6, 1421.

Esaki, N., and Soda, K. (1987). L-methionine gamma-lyase from Pseudomonas putida and Aeromonas. Methods Enzymol 143, 459.

Laemmli, U. K. (1970). Cleavage of structural proteins during the assembly of the head of bacteriophage T4. Nature 227, 680.

Rooseboom, M., Commandeur, J. N. N., and Vermeulen, N. P. E. (2004). Enzyme-catalyzed activation of anticancer prodrugs. Pharm Rev 56, 53.

Sugimura, M., Donato, R., Kakkar, V. V., and Scully, M. F. (1994). Annexin V as a probe of the contribution of anionic phospholipids to the procoagulant activity of tumour cell surfaces. Blood Coagul Fibrinolysis 5, 365.

Utsugi, T., Schroit, A. J., Connor, J., Bucana, C. D., and Fidler, I. J. (1991). Elevated expression of phosphatidylserine in the outer membrane leaflet of human tumor cells and recognition by activated human blood monocytes. Cancer Res 51, 3062.

van Heerde, W. L., Poort, S., van't Veer, C., Reutelingsperger, C. P., and de Groot, P. G. (1994). Binding of recombinant annexin V to endothelial cells: effect of annexin V binding on endothelial-cell-mediated thrombin formation. Biochem J 302 (Pt 1), 305.

van Heerde, W. L., Sakariassen, K. S., Hemker, H. C., Sixma, J. J., Reutelingsperger, C. P., and de Groot, P. G. (1994). Annexin V inhibits the procoagulant activity of matrices of TNF-stimulated endothelium under blood flow conditions. Arterioscler Thromb 14, 824.

Yang, Z., Wang, J., Lu, Q., Xu, J., Kobayashi, Y., Takakura, T., Takimoto, A., Yoshioka, T., Lian, C., Chen, C., Zhang, D., Zhang, Y., Li, S., Sun, X., Tan, Y., Yagi, S., Frenkel, E. P., and Hoffman, R. M. (2004). PEGylation confers greatly extended half-life and attenuated immunogenicity to recombinant methioninase in primates. Cancer Res 64, 6673.

Zang, X. P., Palwai, N. R., Lerner, M. R., Brackett, D. J., Pento, J. T., and Harrison, R. G. (2006). Targeting a methioninase-containing fusion protein to breast cancer urokinase receptors inhibits growth and migration. Anticancer Res 26, 1745.

What is claimed is:

1. A method of treating at least one of a cancer tumor and cancer cells in a patient wherein the cancer tumor/cancer cells is supplied by a tumor vasculature, comprising the step of:
contacting at least one blood vessel supplying a tumor in the patient with a therapeutically effective amount of a conjugate selected from the group consisting of SEQ ID NO:2 and SEQ ID NO:4, the conjugate comprising an annexin having an enzyme operatively attached thereto, wherein the annexin has the ability to specifically and stably bind to at least one of an external receptor and a binding site on an outer surface of a tumor vasculature endothelial cell, wherein the at least one of an external receptor and a binding site is specific to the tumor vasculature endothelial cell, and wherein the enzyme is able to convert a prodrug into an active drug, and whereby the conjugate is maintained on the outer surface of the tumor vasculature endothelial cell;
contacting the at least one blood vessel having the conjugate maintained thereon with a therapeutically effective amount of a selenomethionine prodrug, the selenomethionine prodrug comprising a substrate for the enzyme of the conjugate whereby the selenomethionine prodrug is converted into an active anticancer drug by the enzyme of the conjugate
in close proximity to the tumor vasculature endothelial cell, and wherein the active anticancer drug is carried across the artery wall and travels inside the tumor vasculature endothelial cell by diffusion and permeation flow and directly causes death of the tumor vasculature endothelial cell.

2. The method of claim 1, wherein:
(a) the enzyme is conjugated to polyethylene glycol (PEG); and/or
(b) the conjugate is encapsulated in a liposome.

3. The method of claim 1, further comprising the steps of:
administering a therapeutically effective amount of an immunostimulant to the patient, the immunostimulant selected from the group consisting of glycated chitosan; muramyldipeptide derivatives; trehalose-dimycolates; BCG-cell wall skeleton; various cytokines; and combinations and/or derivatives thereof, and wherein the immunostimulant is effective in enhancing the immune response of the patient to the tumor cells; and
administering a therapeutically effective amount of at least one chemotherapeutic agent to the patient.

4. A method of treating a patient having at least one of a cancer tumor and cancer cells wherein the cancer tumor/cancer cells is supplied by a tumor vasculature, comprising the step of:
administering to a patient a therapeutically effective amount of a conjugate selected from the group consisting of SEQ ID NO:2 and SEQ ID NO:4, the conjugate comprising an annexin having an enzyme operatively attached thereto, wherein the annexin specifically and stably binds to at least one of an external receptor and a binding site on an outer surface of a tumor vasculature endothelial cell of the patient, the at least one of an external receptor and a binding site being specific to the tumor vasculature endothelial cell, and wherein the enzyme is able to convert a prodrug into an active drug, and whereby the conjugate is maintained on the outer surface of the tumor vasculature endothelial cell of the patient;
allowing the free conjugate not bound to a cell to clear from the bloodstream;
administering an effective amount of a selenomethionine prodrug to the patient, the selenomethionine prodrug comprising a substrate for the enzyme of the conjugate, whereby the selenomethionine prodrug comes into contact with the conjugate in close proximity to the tumor vasculature endothelial cell and is converted into an active anticancer drug by the enzyme of the conjugate, and wherein the active anticancer drug is carried across the artery wall and travels inside the tumor vasculature endothelial cell by diffusion and permeation flow and directly causes death of the tumor vasculature endothelial cell of the patient.

5. The method of claim 4, wherein:
(a) the enzyme is conjugated to polyethylene glycol (PEG); and/or
(b) the conjugate is encapsulated in a liposome.

6. The method of claim 4, further comprising the steps of:
administering a therapeutically effective amount of an immunostimulant to the patient, the immunostimulant selected from the group consisting of glycated chitosan; muramyldipeptide derivatives; trehalose-dimycolates; BCG-cell wall skeleton; various cytokines; and combinations and/or derivatives thereof, and wherein the immunostimulant is effective in enhancing the immune response of the patient to the tumor cells; and
administering a therapeutically effective amount of at least one chemotherapeutic agent to the patient.

* * * * *

UNITED STATES PATENT AND TRADEMARK OFFICE
CERTIFICATE OF CORRECTION

Page 1 of 1

PATENT NO. : 8,986,701 B2
APPLICATION NO. : 13/655913
DATED : March 24, 2015
INVENTOR(S) : Roger G. Harrison It is certified that error appears in the above-identified patent and that said Letters Patent is hereby corrected as shown below:

In the Specification:

Column 5, line 11: After "incorporated" insert -- by reference to the same extent as if each individual publication or patent application was specifically and individually indicated to be incorporated by reference. --

Column 9, line 4: After "patent" insert -- Nos. 6,451,312; 6,093,399; 6,004,555; and 6,051,230. The present invention contemplates other tumor/cancer specific external receptors other than anionic phospholipids as targets for the conjugates of the present invention. Such receptors include, for example, those described in U.S. Patent Nos. 6,818,213; 6,783,760; 6,451,312; and 6,406,693. All of the patents, published applications and publications listed herein are hereby expressly incorporated herein by reference in their entireties. --

Signed and Sealed this
Eighteenth Day of August, 2015

Michelle K. Lee
*Director of the United States Patent and Trademark Office*

SEQUENCE LISTING

```
<160> NUMBER OF SEQ ID NOS: 9

<210> SEQ ID NO 1
<211> LENGTH: 2175
<212> TYPE: DNA
<213> ORGANISM: Artificial Sequence
<220> FEATURE:
<223> OTHER INFORMATION: nucleotide sequence encoding a fusion protein
      containing L-methioninase from Pseudomonas putida and human
      annexin V

<400> SEQUENCE: 1
ggaccccgcg actcccataa caacaccggt ttttccacac gggccattca ccacggctac       60
gacccgcttt cccacggtgg tgccttggtg ccaccggtgt accagaccgc gacctatgcc      120
ttcccgactg tcgaatacgg cgctgcgtgc ttcgccgggg aggaggcggg gcacttctac      180
agccgcatct ccaaccccac cctggccttg ctcgagcaac gcatggcctc gttggagggt      240
ggtgaggcgg gattggcgct ggcgtcgggg atgggagcca ttacttcgac cctctggacc      300
ctgctgcggc ctggtgatga gctgatcgtg gggcgcacct tgtatggctg cacctttgcg      360
ttcctgcacc atggcattgg cgagttcggg gtcaagatcc accatgtcga ccttaacgat      420
```

```
gccaaggccc tgaaagcggc gatcaacagc aaaacgcgga tgatctactt cgaaacaccg    480
gccaacccca acatgcaact ggtggatata gcggcggtcg tcgaggcagt gcggggagt    540 gatgtgcttg tggtggtcga caacacctac tgcacgccct acctgcagcg ccactggaa    600 ctggggcag acctggtggt gcattcggcg accaagtacc tcagtggcca tggcgacatc    660
actgcgggcc tggtggtggg gcgcaaggct ttggtcgacc gcattcggct ggaagggctg    720
aaagacatga ccggggcagc cttgtcaccg catgacgctg cgttgttgat gcgcggcatc    780
aagaccctgg cgctgcgcat ggaccggcat tgcgccaacg ccctggaggt cgcgcagttc    840
ctggccgggc agccccaggt ggagctgatc cactacccgg gcttgccgtc gtttgcccag    900
tacgaactgg cacagcggca gatgcgtttg ccgggcggga tgattgcctt tgagctcaag    960
ggcggtatcg aggccgggcg gggcttcatg aatgccctgc agcttttgc ccgtgcggtg   1020 agcctggggg atgccgagtc gctggcacag caccccggcga gcatgacgca ctccagttac   1080
acgccacaag agcgggcgca tcacgggata tcagaggggc tggtgaggtt gtcagtgggg   1140
ctggaggatg tggaggacct gctggcagat atcgagttgg cattggaggc gtgtgcaggc   1200
agcggttctg gatccgcaca ggttctcaga ggcactgtga ctgactgccc tggatttgat   1260
gagcgggctg atgcagaaac tcttcggaag gctatgaaag gcttgggcac agatgaggag   1320
agcatcctga ctctgttgac atcccgaagt aatgctcagc ccaggaaat ctctgcagct   1380 tttaagactc tgtttggcag ggatcttctg gatgacctga atcagaact aactggaaaa   1440 tttgaaaaat taattgtggc tctgatgaaa ccctctcggc tttatgatgc ttatgaactg   1500
aaacatgcct tgaagggagc tggaacaaat gaaaaagtac tgacagaaat tattgcttca   1560
aggacacctg aagaactgag agccatcaaa caagttatg aagaagaata tggctcaagc   1620
ctggaagatg acgtggtggg ggacacttca gggtactacc agcggatgtt ggtggttctc   1680
cttcaggcta acagagaccc tgatgctgga atcgatgaag ctcaagttga acaagatgct   1740
caggctttat ttcaggctgg agaacttaaa tgggggacag atgaagaaaa gtttatcacc   1800
atctttggaa cacgaagtgt gtctcatttg agaaaggtgt ttgacaagta catgactata   1860
tcaggatttc aaattgagga aaccattgac cgcgagactt ctggcaattt agagcaacta   1920
ctccttgctg ttgtgaaatc tattcgaagt atacctgcct accttgcaga gaccctctat   1980
tatgctatga agggagctgg gacagatgat catacccctca tcagagtcat ggtttccagg   2040
agtgagattg atctgtttaa catcaggaag gagtttagga agaattttgc cacctctctt   2100
tattccatga ttaagggaga tacatctggg gactataaga agctcttct gctgctctgt   2160 ggagaagatg actaa                                                     2175
```

<210> SEQ ID NO 2
<211> LENGTH: 724
<212> TYPE: PRT
<213> ORGANISM: Artificial sequence
<220> FEATURE:
<223> OTHER INFORMATION: amino acid sequence of a fusion protein
      containing L-methioninase from Pseudomonas putida and human
      annexin V

<400> SEQUENCE: 2

Gly Pro Arg Asp Ser His Asn Asn Thr Gly Phe Ser Thr Arg Ala Ile
1               5                   10                  15

His His Gly Tyr Asp Pro Leu Ser His Gly Gly Ala Leu Val Pro Pro
            20                  25                  30

Val Tyr Gln Thr Ala Thr Tyr Ala Phe Pro Thr Val Glu Tyr Gly Ala

```
                35                  40                  45
Ala Cys Phe Ala Gly Glu Glu Ala Gly His Phe Tyr Ser Arg Ile Ser
 50                  55                  60

Asn Pro Thr Leu Ala Leu Leu Glu Gln Arg Met Ala Ser Leu Glu Gly
 65                  70                  75                  80

Gly Glu Ala Gly Leu Ala Leu Ala Ser Gly Met Gly Ala Ile Thr Ser
                 85                  90                  95

Thr Leu Trp Thr Leu Leu Arg Pro Gly Asp Glu Leu Ile Val Gly Arg
                100                 105                 110

Thr Leu Tyr Gly Cys Thr Phe Ala Phe Leu His His Gly Ile Gly Glu
                115                 120                 125

Phe Gly Val Lys Ile His His Val Asp Leu Asn Asp Ala Lys Ala Leu
130                 135                 140

Lys Ala Ala Ile Asn Ser Lys Thr Arg Met Ile Tyr Phe Glu Thr Pro
145                 150                 155                 160

Ala Asn Pro Asn Met Gln Leu Val Asp Ile Ala Ala Val Val Glu Ala
                165                 170                 175

Val Arg Gly Ser Asp Val Leu Val Val Asp Asn Thr Tyr Cys Thr
                180                 185                 190

Pro Tyr Leu Gln Arg Pro Leu Glu Leu Gly Ala Asp Leu Val Val His
                195                 200                 205

Ser Ala Thr Lys Tyr Leu Ser Gly His Gly Asp Ile Thr Ala Gly Leu
210                 215                 220

Val Val Gly Arg Lys Ala Leu Val Asp Arg Ile Arg Leu Glu Gly Leu
225                 230                 235                 240

Lys Asp Met Thr Gly Ala Ala Leu Ser Pro His Asp Ala Ala Leu Leu
                245                 250                 255

Met Arg Gly Ile Lys Thr Leu Ala Leu Arg Met Asp Arg His Cys Ala
                260                 265                 270

Asn Ala Leu Glu Val Ala Gln Phe Leu Ala Gly Gln Pro Gln Val Glu
                275                 280                 285

Leu Ile His Tyr Pro Gly Leu Pro Ser Phe Ala Gln Tyr Glu Leu Ala
                290                 295                 300

Gln Arg Gln Met Arg Leu Pro Gly Gly Met Ile Ala Phe Glu Leu Lys
305                 310                 315                 320

Gly Gly Ile Glu Ala Gly Arg Gly Phe Met Asn Ala Leu Gln Leu Phe
                325                 330                 335

Ala Arg Ala Val Ser Leu Gly Asp Ala Glu Ser Leu Ala Gln His Pro
                340                 345                 350

Ala Ser Met Thr His Ser Ser Tyr Thr Pro Gln Glu Arg Ala His His
                355                 360                 365

Gly Ile Ser Glu Gly Leu Val Arg Leu Ser Val Gly Leu Glu Asp Val
                370                 375                 380

Glu Asp Leu Leu Ala Asp Ile Glu Leu Ala Leu Glu Ala Cys Ala Gly
385                 390                 395                 400

Ser Gly Ser Gly Ser Ala Gln Val Leu Arg Gly Thr Val Thr Asp Cys
                405                 410                 415

Pro Gly Phe Asp Glu Arg Ala Asp Ala Glu Thr Leu Arg Lys Ala Met
                420                 425                 430

Lys Gly Leu Gly Thr Asp Glu Glu Ser Ile Leu Thr Leu Leu Thr Ser
                435                 440                 445

Arg Ser Asn Ala Gln Arg Gln Glu Ile Ser Ala Ala Phe Lys Thr Leu
450                 455                 460
```

Phe Gly Arg Asp Leu Leu Asp Leu Lys Ser Glu Leu Thr Gly Lys
465                 470                 475                 480

Phe Glu Lys Leu Ile Val Ala Leu Met Lys Pro Ser Arg Leu Tyr Asp
            485                 490                 495

Ala Tyr Glu Leu Lys His Ala Leu Lys Gly Ala Gly Thr Asn Glu Lys
                500                 505                 510

Val Leu Thr Glu Ile Ile Ala Ser Arg Thr Pro Glu Glu Leu Arg Ala
            515                 520                 525

Ile Lys Gln Val Tyr Glu Glu Tyr Gly Ser Ser Leu Glu Asp Asp
            530                 535                 540

Val Val Gly Asp Thr Ser Gly Tyr Tyr Gln Arg Met Leu Val Val Leu
545                 550                 555                 560

Leu Gln Ala Asn Arg Asp Pro Asp Ala Gly Ile Asp Glu Ala Gln Val
                565                 570                 575

Glu Gln Asp Ala Gln Ala Leu Phe Gln Ala Gly Glu Leu Lys Trp Gly
                580                 585                 590

Thr Asp Glu Glu Lys Phe Ile Thr Ile Phe Gly Thr Arg Ser Val Ser
            595                 600                 605

His Leu Arg Lys Val Phe Asp Lys Tyr Met Thr Ile Ser Gly Phe Gln
            610                 615                 620

Ile Glu Glu Thr Ile Asp Arg Glu Thr Ser Gly Asn Leu Glu Gln Leu
625                 630                 635                 640

Leu Leu Ala Val Val Lys Ser Ile Arg Ser Ile Pro Ala Tyr Leu Ala
                645                 650                 655

Glu Thr Leu Tyr Tyr Ala Met Lys Gly Ala Gly Thr Asp Asp His Thr
                660                 665                 670

Leu Ile Arg Val Met Val Ser Arg Ser Glu Ile Asp Leu Phe Asn Ile
            675                 680                 685

Arg Lys Glu Phe Arg Lys Asn Phe Ala Thr Ser Leu Tyr Ser Met Ile
            690                 695                 700

Lys Gly Asp Thr Ser Gly Asp Tyr Lys Lys Ala Leu Leu Leu Leu Cys
705                 710                 715                 720

Gly Glu Asp Asp

<210> SEQ ID NO 3
<211> LENGTH: 2175
<212> TYPE: DNA
<213> ORGANISM: Artificial sequence
<220> FEATURE:
<223> OTHER INFORMATION: nucleotide sequence encoding a fusion protein
      containing L-methioninase from Pseudomonas putida and human
      annexin V

<400> SEQUENCE: 3
ggaccccgcg actcccataa caacaccggt tttgccacac gggccattca ccacggctac      60
gacccgcttt cccacggtgg tgccttggtg ccaccggtgt accagaccgc gacctatgcc     120
ttcccgactg tcgaatacgg cgctgcgtgc ttcgccgggg aggaggcggg gcacttctac     180
agccgcatct ccaaccccac cctggccttg ctcgagcaac gcatggcctc gttggagggt     240
ggtgaggcgg gattggcgct ggcgtcgggg atgggagcca ttacttcgac cctctggacc     300
ctgctgcggc ctggtgatga gctgatcgtg gggcgcacct tgtatggctg caccttttgcg    360 ttcctgcacc atggcattgg cgagttcggg gtcaagatcc accatgtcga ccttaacgat     420
gccaaggccc tgaaagcggc gatcaacagc aaaacgcgga tgatctactt cgaaacaccg     480

```
gccaacccca acatgcaact ggtggatata gcggcggtcg tcgaggcagt gcggggagt      540 gatgtgcttg tggtggtcga caacacctac tgcacgccct acctgcagcg gccactggaa    600
ctgggggcag acctggtggt gcattcggcg accaagtacc tcagtggcca tggcgacatc    660
actgcgggcc tggtggtggg cgcaaggct ttggtcgacc gcattcggct ggaagggctg     720
aaagacatga ccggggcagc cttgtcaccg catgacgctg cgttgttgat gcgcggcatc    780
aagaccctgg cgctgcgcat ggaccggcat tgcgccaacg ccctggaggt cgcgcagttc    840
ctggccgggc agccccaggt ggagctgatc cactacccgg gcttgccgtc gtttgcccag    900
tacgaactgg cacagcggca gatgcgtttg ccgggcggga tgattgcctt tgagctcaag    960
ggcggtatcg aggccgggcg gggcttcatg aatgccctgc agcttttgc ccgtgcggtg    1020 agcctggggg atgccgagtc gctggcacag caccggcga gcatgacgca ctccagttac    1080
acgccacaag agcgggcgca tcacgggata tcagaggggc tggtgaggtt gtcagtgggg    1140
ctggaggatg tggaggacct gctggcagat atcgagttgg cattggaggc gtgtgcaggc    1200
agcggttctg gatccgcaca ggttctcaga ggcactgtga ctgacttccc tggatttgat    1260
gagcgggctg atgcagaaac tcttcggaag gctatgaaag gcttgggcac agatgaggag    1320
agcatcctga ctctgttgac atcccgaagt aatgctcagc gccaggaaat ctctgcagct    1380
tttaagactc tgtttggcag ggatcttctg gatgacctga atcagaact aactggaaaa     1440 tttgaaaaat taattgtggc tctgatgaaa ccctctcggc tttatgatgc ttatgaactg    1500
aaacatgcct tgaagggagc tggaacaaat gaaaagtac tgacagaaat tattgcttca    1560
aggacacctg aagaactgag agccatcaaa caagtttatg aagaagaata tggctcaagc    1620
ctggaagatg acgtggtggg ggacacttca gggtactacc agcggatgtt ggtggttctc    1680
cttcaggcta acagagaccc tgatgctgga atcgatgaag ctcaagttga acaagatgct    1740
caggctttat ttcaggctgg agaacttaaa tgggggacag atgaagaaaa gtttatcacc    1800
atctttggaa cacgaagtgt gtctcatttg agaaaggtgt ttgacaagta catgactata    1860
tcaggatttc aaattgagga aaccattgac cgcgagactt ctggcaattt agagcaacta    1920
ctccttgctg ttgtgaaatc tattcgaagt atacctgcct accttgcaga gcccctctat    1980
tatgctatga agggagctgg acagatgat catacccctca tcagagtcat ggtttccagg    2040
agtgagattg atctgtttaa catcaggaag gagtttagga agaattttgc cacctctctt    2100
tattccatga ttaagggaga tacatctggg gactataaga aagctcttct gctgctctgt    2160
ggagaagatg actaa                                                      2175
```

<210> SEQ ID NO 4
<211> LENGTH: 724
<212> TYPE: PRT
<213> ORGANISM: Artificial sequence
<220> FEATURE:
<223> OTHER INFORMATION: amino acid sequence of a fusion protein
      containing L-methioninase from Pseudomonas putida and human
      annexin V

<400> SEQUENCE: 4

Gly Pro Arg Asp Ser His Asn Asn Thr Gly Cys Ser Thr Arg Ala Ile
1               5                   10                  15

His His Gly Tyr Asp Pro Leu Ser His Gly Gly Ala Leu Val Pro Pro
            20                  25                  30

Val Tyr Gln Thr Ala Thr Tyr Ala Phe Pro Thr Val Glu Tyr Gly Ala
        35                  40                  45

```
Ala Cys Phe Ala Gly Glu Glu Ala Gly His Phe Tyr Ser Arg Ile Ser
 50                  55                  60

Asn Pro Thr Leu Ala Leu Leu Glu Gln Arg Met Ala Ser Leu Glu Gly
 65                  70                  75                  80

Gly Glu Ala Gly Leu Ala Leu Ala Ser Gly Met Gly Ala Ile Thr Ser
                 85                  90                  95

Thr Leu Trp Thr Leu Arg Pro Gly Asp Glu Leu Ile Val Gly Arg
            100                 105                 110

Thr Leu Tyr Gly Cys Thr Phe Ala Phe Leu His His Gly Ile Gly Glu
        115                 120                 125

Phe Gly Val Lys Ile His His Val Asp Leu Asn Asp Ala Lys Ala Leu
    130                 135                 140

Lys Ala Ala Ile Asn Ser Lys Thr Arg Met Ile Tyr Phe Glu Thr Pro
145                 150                 155                 160

Ala Asn Pro Asn Met Gln Leu Val Asp Ile Ala Ala Val Val Glu Ala
                165                 170                 175

Val Arg Gly Ser Asp Val Leu Val Val Asp Asn Thr Tyr Cys Thr
            180                 185                 190

Pro Tyr Leu Gln Arg Pro Leu Glu Leu Gly Ala Asp Leu Val Val His
        195                 200                 205

Ser Ala Thr Lys Tyr Leu Ser Gly His Gly Asp Ile Thr Ala Gly Leu
    210                 215                 220

Val Val Gly Arg Lys Ala Leu Val Asp Arg Ile Arg Leu Glu Gly Leu
225                 230                 235                 240

Lys Asp Met Thr Gly Ala Ala Leu Ser Pro His Asp Ala Ala Leu Leu
                245                 250                 255

Met Arg Gly Ile Lys Thr Leu Ala Leu Arg Met Asp Arg His Cys Ala
            260                 265                 270

Asn Ala Leu Glu Val Ala Gln Phe Leu Ala Gly Gln Pro Gln Val Glu
        275                 280                 285

Leu Ile His Tyr Pro Gly Leu Pro Ser Phe Ala Gln Tyr Glu Leu Ala
    290                 295                 300

Gln Arg Gln Met Arg Leu Pro Gly Gly Met Ile Ala Phe Glu Leu Lys
305                 310                 315                 320

Gly Gly Ile Glu Ala Gly Arg Gly Phe Met Asn Ala Leu Gln Leu Phe
                325                 330                 335

Ala Arg Ala Val Ser Leu Gly Asp Ala Glu Ser Leu Ala Gln His Pro
            340                 345                 350

Ala Ser Met Thr His Ser Ser Tyr Thr Pro Gln Glu Arg Ala His His
        355                 360                 365

Gly Ile Ser Glu Gly Leu Val Arg Leu Ser Val Gly Leu Glu Asp Val
    370                 375                 380

Glu Asp Leu Leu Ala Asp Ile Glu Leu Ala Leu Glu Ala Cys Ala Gly
385                 390                 395                 400

Ser Gly Ser Gly Ser Ala Gln Val Leu Arg Gly Thr Val Thr Asp Phe
                405                 410                 415

Pro Gly Phe Asp Glu Arg Ala Asp Ala Glu Thr Leu Arg Lys Ala Met
            420                 425                 430

Lys Gly Leu Gly Thr Asp Glu Ser Ile Leu Thr Leu Leu Thr Ser
        435                 440                 445

Arg Ser Asn Ala Gln Arg Gln Glu Ile Ser Ala Ala Phe Lys Thr Leu
450                 455                 460

Phe Gly Arg Asp Leu Leu Asp Asp Leu Lys Ser Glu Leu Thr Gly Lys
```

```
            465             470              475            480
    Phe Glu Lys Leu Ile Val Ala Leu Met Lys Pro Ser Arg Leu Tyr Asp
                        485             490              495

Ala Tyr Glu Leu Lys His Ala Leu Lys Gly Ala Gly Thr Asn Glu Lys
                    500             505              510

Val Leu Thr Glu Ile Ile Ala Ser Arg Thr Pro Glu Leu Arg Ala
                515             520              525

Ile Lys Gln Val Tyr Glu Glu Tyr Gly Ser Ser Leu Glu Asp Asp
            530             535              540

Val Val Gly Asp Thr Ser Gly Tyr Tyr Gln Arg Met Leu Val Val Leu
    545             550              555             560

Leu Gln Ala Asn Arg Asp Pro Asp Ala Gly Ile Asp Glu Ala Gln Val
                    565             570              575

Glu Gln Asp Ala Gln Ala Leu Phe Gln Ala Gly Glu Leu Lys Trp Gly
                580             585              590

Thr Asp Glu Glu Lys Phe Ile Thr Ile Phe Gly Thr Arg Ser Val Ser
                595             600              605

His Leu Arg Lys Val Phe Asp Lys Tyr Met Thr Ile Ser Gly Phe Gln
            610             615              620

Ile Glu Glu Thr Ile Asp Arg Glu Thr Ser Gly Asn Leu Glu Gln Leu
    625             630              635             640

Leu Leu Ala Val Val Lys Ser Ile Arg Ser Ile Pro Ala Tyr Leu Ala
                    645             650              655

Glu Thr Leu Tyr Tyr Ala Met Lys Gly Ala Gly Thr Asp Asp His Thr
                660             665              670

Leu Ile Arg Val Met Val Ser Arg Ser Glu Ile Asp Leu Phe Asn Ile
                675             680              685

Arg Lys Glu Phe Arg Lys Asn Phe Ala Thr Ser Leu Tyr Ser Met Ile
                690             695              700

Lys Gly Asp Thr Ser Gly Asp Tyr Lys Lys Ala Leu Leu Leu Leu Cys
    705             710              715             720

Gly Glu Asp Asp

<210> SEQ ID NO 5
<211> LENGTH: 60
<212> TYPE: DNA
<213> ORGANISM: Artificial Sequence
<220> FEATURE:
<223> OTHER INFORMATION: 5' primer for L-methioninase

<400> SEQUENCE: 5
gacgacgaca agatgcttga agtcctcttt cagggacccc gcgactccca taccaacacc    60

<210> SEQ ID NO 6
<211> LENGTH: 51
<212> TYPE: DNA
<213> ORGANISM: Artificial sequence
<220> FEATURE:
<223> OTHER INFORMATION: 3' primer for L-methioninase

<400> SEQUENCE: 6
gccgcattgg atccagaacc gctgcctgca cacgcctcca acgccaactc g             51

<210> SEQ ID NO 7
<211> LENGTH: 32
<212> TYPE: DNA
<213> ORGANISM: Artificial Sequence
<220> FEATURE:
```

```
<223> OTHER INFORMATION: 5' primer for Annexin V

<400> SEQUENCE: 7
cgattcgcgg atccgcacag gttctcagag gc                              32

<210> SEQ ID NO 8
<211> LENGTH: 36
<212> TYPE: DNA
<213> ORGANISM: Artificial Sequence
<220> FEATURE:
<223> OTHER INFORMATION: 3' primer for Annexin V

<400> SEQUENCE: 8
gaggagaagc ccggttagtc atcttctcca cagagc                          36

<210> SEQ ID NO 9
<211> LENGTH: 10
<212> TYPE: PRT
<213> ORGANISM: Artificial sequence
<220> FEATURE:
<223> OTHER INFORMATION: synthetic peptide

<400> SEQUENCE: 9

Cys Thr Thr His Trp Gly Phe Thr Leu Cys
1               5                   10
```